US007074778B2

(12) United States Patent
Levitt et al.

(10) Patent No.: US 7,074,778 B2
(45) Date of Patent: Jul. 11, 2006

(54) ASTHMA ASSOCIATED FACTORS AS TARGETS FOR TREATING ATOPIC ALLERGIES INCLUDING ASTHMA AND RELATED DISORDERS

(75) Inventors: Roy C. Levitt, Plymouth Meeting, PA (US); Nicholas C. Nicolaides, Plymouth Meeting, PA (US); William A. Kinney, Plymouth Meeting, PA (US); Steve Jones, Plymouth Meeting, PA (US)

(73) Assignee: Genaera Corporation, Plymouth Meeting, PA (US)

(*) Notice: Subject to any disclaimer, the term of this patent is extended or adjusted under 35 U.S.C. 154(b) by 170 days.

(21) Appl. No.: 10/148,553

(22) PCT Filed: Dec. 11, 2000

(86) PCT No.: PCT/US00/33526

§ 371 (c)(1),
(2), (4) Date: Oct. 9, 2002

(87) PCT Pub. No.: WO01/42273

PCT Pub. Date: Jun. 14, 2001

(65) Prior Publication Data

US 2003/0232791 A1 Dec. 18, 2003

Related U.S. Application Data

(60) Provisional application No. 60/169,959, filed on Dec. 9, 1999.

(51) Int. Cl.
*A61K 31/575* (2006.01)
*A61K 31/58* (2006.01)
*C07J 41/00* (2006.01)
*C07J 43/00* (2006.01)

(52) U.S. Cl. .............. 514/169; 514/175; 514/176; 514/182; 514/826; 540/97; 540/109; 540/112; 540/115; 552/548; 552/551; 552/553; 552/554

(58) Field of Classification Search ............... 514/175, 514/176, 182, 169, 826; 540/97, 109, 112, 540/115; 552/551, 554, 548, 553
See application file for complete search history.

(56) References Cited

U.S. PATENT DOCUMENTS

| 5,250,524 | A | * | 10/1993 | Kramer et al. | 514/177 |
|---|---|---|---|---|---|
| 5,637,691 | A | | 6/1997 | Frye et al. | 540/106 |
| 5,721,226 | A | | 2/1998 | Frye et al. | 514/169 |
| 5,733,899 | A | | 3/1998 | Frye et al. | 514/169 |
| 5,763,430 | A | | 6/1998 | Zasloff | 514/169 |
| 5,792,635 | A | | 8/1998 | Zasloff | 435/184 |
| 5,795,885 | A | | 8/1998 | Zasloff et al. | 514/182 |
| 5,840,740 | A | | 11/1998 | Zasloff et al. | 514/182 |
| 5,840,936 | A | | 11/1998 | Zasloff et al. | 552/521 |
| 5,847,172 | A | | 12/1998 | Zasloff et al. | 552/521 |
| 5,856,535 | A | | 1/1999 | Zasloff et al. | 552/521 |
| 5,874,597 | A | | 2/1999 | Jones | 552/521 |
| 5,908,839 | A | * | 6/1999 | Levitt et al. | 514/182 |
| 5,994,336 | A | | 11/1999 | Zasloff et al. | 514/182 |
| 2002/0156013 | A1 | * | 10/2002 | Renauld et al. | |

FOREIGN PATENT DOCUMENTS

WO  WO 99/14242  *  3/1999

OTHER PUBLICATIONS

Burrows et al. (1989) Association of asthma with serum IgE levels and skin-test reactivity to allergens, N. Engl. J. Med. 320:271-277.
Burrows et al. (1992) Relationships of bronchial responsiveness assessed by methacholine to serum IgE, lung function, symptoms, and diagnoses in 11-year-old New Zealand children, J. Allergy Clin. Immunol. 90:376-385.
Chang et al. (1994) Isolation and characterization of the human interleukin-9 receptor gene, Blood 83:3199-3205.
Clifford et al. (1987) Symptoms, atopy, and bronchial response to methacholine in parents with asthma and their children, Arch. Dis. Child. 62:66-73.
Doull et al. (1996) Allelic association of gene markers on chromosomes 5q and 11q with atopy and bronchial hyperresponsiveness, Am. J. Respir. Crit. Care Med. 153:1280-1284.
Dugas et al. (1993) Interleukin-9 potentiates the interleukin-4-induced immunoglobulin (IgG, IgM and IgE) production by normal human B lymphocytes, Eur. J. Immunol. 23:1687-1692.
Eklund et al. (1993) Induction by IL-9 and suppression by IL-3 and IL-4 of the levels of chromosome 14-derived transcripts that encode late-expressed mouse mast cell proteases, J. Immunol. 151:4266-4273.
Gergen et al. (1991) The association of allergen skin test reactivity and respiratory disease among whites in the US population. Data from the Second National Health and Nutrition Examination Survey, 1976 to 1980, Arch. Intern. Med. 151:487-492.

(Continued)

Primary Examiner—Barbara P. Badio
(74) Attorney, Agent, or Firm—Morgan, Lewis & Bockius LLP

(57) ABSTRACT

This invention relates to methods for treating asthma or allergy in a mammal by administering a 3-aminosteroid compound to a mammal in need thereof. The 3-aminosteroid compound being capable of down regulating the IL-9 pathway and alleviating asthmatic responses to allergen. Exemplary 3-aminosteroid compounds used in the methods of the invention include compounds having the chemical formula (I), wherein X, $R^1$, $R^2$, $R^3$, and $R^4$ groups are as defined herein. The invention also relates to certain novel compounds of formula (I). Moreover, the invention also provides methods for identifying an immunomodulatory 3-aminosteroid compound.

7 Claims, 23 Drawing Sheets

OTHER PUBLICATIONS

Halonen et al. (1992) The predictive relationship between serum IgE levels at birth and subsequent incidences of lower respiratory illnesses and eczema in infants, Am. Rev. Respir. Dis. 146:866-870.

Houssiau et al. (1995) A cascade of cytokines is responsible for IL-9 expression in human T cells. Involvement of IL-2, IL-4, and IL-10, J. Immunol. 154:2624-2630.

Johannson et al. (1972) The clinical significance of IgE, Prog. Clin. Immunol. 1:157-181.

Jones et al. (1996) The synthesis and characterization of analogs of the antimicrobial compound squalamine: 6-beta-hydroxy-3-aminosterols synthesized from hyodeoxycholic acid, Steroids 61:565-571.

Kelleher et al. (1991) Human interleukin-9: genomic sequence, chromosomal location, and sequences essential for its expression in human T-cell leukemia virus (HTLV)-I-transformed human T cells, Blood 77:1436-1441.

Levitt et al. (1995) Linkage homology for bronchial hyper-responsiveness between DNA markers on human chromosome 5q31-q33 and mouse chromosome 13, Clin. Exp. Allergy 25 (Suppl) 2:61-63.

Louahed et al. (1995) IL-9 induces expression of granzymes and high-affinity IgE receptor in murine T helper clones, J. Immunol. 154:5061-5070.

Miyazawa et al. (1992) Recombinant human interleukin-9 induces protein tyrosine phosphorylation and synergizes with steel factor to stimulate proliferation of the human factor-dependent cell line, M07e, Blood 80:1685-1692.

Nicolaides et al. (1997) Interleukin 9: a candidate gene for asthma, Proc. Natl. Acad. Sci. USA 94:13175-13180.

Petit-Frere et al. (1993) Interleukin-9 potentiates the interleukin-4-induced IgE and IgG1 release from murine B lymphocytes, Immunology 79:146-151.

Postma et al. (1995) Genetic susceptibility to asthma- bronchial hyperresponsiveness coinherited with a major gene for atopy, N. Engl. J. Med. 333:894-900.

Rao et al. (1997) Practical approaches to remote asymmetric induction in steroidal side-chains utilizing oxazaborolidine reagents, J. Org. Chem. 62:4541-4545.

Renauld et al. (1990) Human P40/IL-9. Expression in activated CD4+ T cells, genomic organization, and comparison with the mouse gene, J. Immunol. 144:4235-4241.

Renauld et al. (1992) Expression cloning of murine and human interleukin 9 receptor cDNAs, Proc. Natl. Acad. Sci. USA. 89:5690-5694.

Sears et al. (1991) Relation between airway responsiveness and serum IgE in children with asthma and in apparently normal children, N. Engl. J. Med. 325:1067-1071.

Yin et al. (1994) JAK1 kinase forms complexes with interleukin-4 receptor and 4PS/insulin receptor substrate-1-like protein and is activated by interleukin-4 and interleukin-9 in T lymphocytes, J. Biol. Chem. 269:26614-26617.

* cited by examiner

Name and Chemical Structure of Aminosterols

1. 1505

2. preSQLS-658 (not determined)

3. 1360

4. 1361

5. preSQHS-642 (not determined)

6. preSQHS-781 (not determined)

7. dessulfateSQ (not determined)

Q

Novel Aminosteroids with Ester Isoteres

R2= H, OH, OAc,

R3= H, OH, OAc,

R4= H, OH, OAc,

R5= $C_1$ to $C_{12}$ alkyl.

R6= H, C1 to C6 alkyl, phenyl.

R7= H, C1 to C6 alkyl, phenyl.

R8= H, C1 to C6 alkyl, phenyl.

R1=

Novel Aminosteroid Esters with Modified Polyamines x = { -CH$_2$-CO$_2$R5 .

R2= H, OH, OAc, {–C(O)–R7 .

R3= H, OH, OAc, {–C(O)–R7 .

R4= H, OH, OAc, {–C(O)–R7 .

R5= C$_1$ to C$_{12}$ alkyl.

R6= H, C1 to C6 alkyl, phenyl.

R7= H, C1 to C6 alkyl, phenyl.

R1= R6-NH$_2$- }

Novel Acylated Aminosteroid Esters

R2= H, OAc, $\{\overset{O}{\underset{}{\text{−C−R7}}}$ .

R3= H, OAc, $\{\overset{O}{\underset{}{\text{−C−R7}}}$ .

R4= H, OAc, $\{\overset{O}{\underset{}{\text{−C−R7}}}$ .

R1= $H_2N\frown N\frown \}$

R5= $C_1$ to $C_{12}$ alkyl.

R7= H, C1 to C6 alkyl, phenyl.

At least one of R2, R3, or R4 is $\{\overset{O}{\underset{}{\text{−C−R7}}}$ .

Effects of Immunostimulatory Aminosteroids on IL-9 Expression in Mitogen-Stimulated Human Lymphocytes

ASTHMA ASSOCIATED FACTORS AS TARGETS FOR TREATING ATOPIC ALLERGIES INCLUDING ASTHMA AND RELATED DISORDERS

CROSS REFERENCE TO RELATED APPLICATION

This application is a 371 of PCT/US00/33526 filed Dec. 11, 2000 and claims the benefit of U.S. Provisional Application 60/169,959 filed Dec. 9, 1999, which is herein incorporated by reference in its entirety. This application is related to U.S. application Ser. No. 09/325,571 filed Jun. 4, 1999, now U.S. Pat. No. 6,261,559 which is a continuation of U.S. application Ser. No. 08/874,503 filed Jun. 13, 1997, now abandoned, which claims the benefit of U.S. Provisional Application 60/002,765 filed Aug. 24, 1995 all of which are herein incorporated by reference in their entirety. This application is also related to U.S. application Ser. No. 09/198,486 filed Nov. 24, 1998, now abandoned; U.S. application Ser. No. 08/769,689 filed Dec. 18, 1996 now U.S. Pat. No. 5,856,535; and U.S. application Ser. No. 08/478,763 filed Jun. 7, 1995 now U.S. Pat. No. 5,721,226 all of which are herein incorporated by reference in their entirety.

FIELD OF THE INVENTION

This invention relates to methods for treating atopic allergies and related disorders, such as asthma, in a mammal. More particularly, the invention relates to methods for regulating IL-9 activity in a mammal by administering a 3-aminosteroid compound that down regulates the IL-9 pathway and asthmatic responses to allergen. The invention also relates to certain novel 3-aminosteroid compounds. In addition, the invention also provides methods for identifying immunomodulatory 3-aminosteroid compounds.

BACKGROUND OF THE INVENTION

Inflammation is a complex process in which the body's defense system combats foreign entities. While the battle against foreign entities may be necessary for the body's survival, some defense systems respond to foreign entities, even innocuous ones, as dangerous and thereby damage surrounding tissue in the ensuing conflict.

Atopic allergy or atopy, is an ecogenetic disorder, where genetic background dictates the response to environmental stimuli, such as pollen, food, dander and insect venoms. The disorder is generally characterized by an increased ability of lymphocytes to produce IgE antibodies in response to ubiquitous antigens. Activation of the immune system by these antigens leads to allergic inflammation and may occur after ingestion, penetration through the skin or after inhalation. When this immune activation occurs and is accompanied by pulmonary inflammation and bronchial hyperresponsiveness, this disorder is broadly characterized as asthma. Many cell types are involved in this inflammatory reaction and they include T cells and antigen-presenting cells, B cells that produce IgE and basophils and eosinophils that bind IgE. These inflammatory cells accumulate at the site of allergic inflammation and the toxic products they release contribute to tissue destruction related to these disorders.

While asthma is generally defined as an inflammatory disorder of the airways, clinical symptoms arise from intermittent air flow obstruction. It is a chronic, disabling disorder that appears to be increasing in prevalence and severity (Gergen et al., (1992) Am. Rev. Respir. Dis. 146, 823–824). It is estimated that 30–40% of the population suffer with atopic allergy and 15% of children and 5% of adults in the population suffer from asthma (Gergen et al., (1992) Am. Rev. Respir. Dis. 146, 823–824). Thus, an enormous burden is placed on our health-care resources.

Interestingly, while most individuals experience similar environmental exposures, only certain individuals develop atopic allergy and asthma. This hypersensitivity to environmental allergens known as atopy, is often indicated by elevated serum IgE levels or abnormally intense skin test response to allergens in atopic individuals as compared to non-atopics (Marsh et al., (1982) New Eng. J. Med. 305, 1551–1559). Strong evidence for a close relationship between atopic allergy and asthma is derived from the fact that most asthmatics have clinical and serologic evidence of atopy (Clifford et al., (1987) Arch. Dis. Childhood 62, 66–73; Gergen, (1991) Arch. Intern. Med. 151, 487–492; Burrows et al., (1992) J. Allergy Clin. Immunol. 90, 376–385; Johannson et al., (1972) Prog. Clin. Immunol. 1, 1–25; Sears et al., (1991) New Engl. J. Med. 325. 1067–1071; Halonen et al., (1992) Am. Rev. Respir. Dis. 146, 666–670). In particular, younger asthmatics have a high incidence of atopy (Marsh et al., (1982) New Eng. J. Med. 305, 1551–1559). In addition, immunologic factors associated with an increase in total serum IgE levels are very closely related to impaired pulmonary function (Burrows et al., (1989) New Eng. J. Med. 320, 271–277).

Both the diagnosis and treatment of these disorders are problematic (Gergen et al., (1992) Am. Rev. Respir. Dis. 146, 823–824). The assessment of inflamed lung tissue is often difficult and frequently the source of the inflammation cannot be determined. Without knowledge of the source of the airway inflammation and protection from the inciting foreign environmental agent or agents, the inflammatory process cannot be interrupted. It is now generally accepted that failure to control pulmonary inflammation leads to significant loss of lung function over time.

Current treatments suffer from their own set of disadvantages. The main therapeutic agents, beta receptor agonists, reduce the symptoms thereby transiently improving pulmonary function, but do not affect the underlying inflammation so that lung tissue remains in jeopardy. In addition, constant use of beta receptor agonists results in desensitization which reduces their efficacy and safety (Molinoff et al., (1995) Goodman and Gilman's The Pharmacologic Basis of Therapeutics, MacMillan Publishing). The agents that can diminish the underlying inflammation, the anti-inflammatory steroids, have their own list of disadvantages that range from immunosuppression to bone loss (Molinoff et al., (1995) Goodman and Gilman's The Pharmacologic Basis of Therapeutics, MacMillan Publishing).

Because of the problems associated with conventional therapies, alternative treatment strategies have been evaluated. Glycophorin A (Chu et al., (1992) Cell. Immunol. 145, 223–239), cyclosporin (Alexander et al., (1992) Lancet 339, 324–328; Morely, (1992) J. Autoimmun. 5 Suppl A, 265–269) and a nonapeptide fragment of interleukin 2 (IL-2) (Zavyalov et al., (1992) Immunol. Lett. 31, 285–288) all inhibit potentially critical immune functions associated with homeostasis. What is needed in the art is a treatment for asthma that addresses the underlying pathogenesis. Moreover, these therapies should address the episodic nature of the disorder and the close association with allergy and intervene at a point downstream from critical immune functions.

In the related patent applications mentioned above, applicants have demonstrated that interleukin 9 (IL-9), its receptor and activities effected by IL-9 are the appropriate targets for therapeutic intervention in atopic allergy, asthma and related disorders.

Mediator release from mast cells by allergen has long been considered a critical initiating event in allergy. IL-9 was originally identified as a mast cell growth factor and it has been demonstrated that IL-9 up-regulates the expression of mast cell proteases including MCP-1, MCP-2, MCP-4 (Eklund et al., (1993) J. Immunol. 151, 4266–4273) and granzyme B (Louahed et al., (1995) J. Immunol. 154. 5061–5070). Thus, IL-9 appears to serve a role in the proliferation and differentiation of mast cells. Moreover, IL-9 up-regulates the expression of the alpha chain of the high affinity IgE receptor (Dugas et al., (1993) Eur. J. Immunol. 23, 1687–1692). Elevated IgE levels are considered to be a hallmark of atopic allergy and a risk factor for asthma. Furthermore, both in vitro and in vivo studies have shown IL-9 to potentiate the release of IgE from primed B cells (Petit-Frere et al., (1993) Immunology 79, 146–151).

There is substantial support for the role of IL-9 gene in asthma. First, linkage homology between humans and mice suggests that the same gene is responsible for producing biologic variability in response to antigen in both species. Second, differences in expression of the murine IL-9 candidate gene are associated with biologic variability in bronchial responsiveness. In particular, reduced expression of IL-9 is associated with a lower baseline bronchial response in B6 mice (Nicolaides et al., (1997) Proc. Natl. Acad. Sci. USA 94, 13175–13180). Third, recent evidence for linkage disequilibrium in data from humans suggests IL-9 may be associated with atopy and bronchial hyperresponsiveness consistent with a role for this gene in both species (Doull et al., (1996) Am. J. Respir. Crit. Care Med. 153, 1280–1284). Moreover, a genetic alteration in the human gene appears to be associated with loss of cytokine function and lower IgE levels. Fourth, the pleiotropic functions of this cytokine and its receptor in the allergic immune response strongly support a role for the IL-9 pathway in the complex pathogenesis of asthma. Fifth, in humans, biologic variability in the IL-9 receptor also appears to be associated with atopic allergy and asthma. Finally, despite the inherited loss of IL-9 receptor function, these individuals appear to be otherwise healthy. Thus, nature has demonstrated in atopic individuals that the therapeutic down-regulation of IL-9 and IL-9 receptor genes or genes activated by IL-9 and its receptor is likely to be safe.

Airway hyperresponsiveness is found in virtually all asthmatics and in some strains of inbred mice (DBA2) (Levitt et al., (1995) Clin. Exp. Allergy 25, 61–63). Airway hyperresponsiveness is a risk factor for the development of asthma in humans and is used in animal models of asthma as a physiologic measure to assess the efficacy of treatment for asthma. This data along with human (Postma et al., (1995) New Engl. J. Med. 333, 894–900) and murine genetic mapping results (U.S. Pat. No. 5,908,839) suggests a critical role for the murine IL-9 gene product in the airway response of the mouse. In particular, the bronchial hyperresponsive DBA2 mice differ from the C57BL6 hyporesponsive mice (Nicolaides et al., (1997) Proc. Natl. Acad. Sci. USA 94, 13175–13180) in their expression of steady state levels of IL-9 (U.S. Pat. No. 5,908,839). Furthermore, pretreatment with blocking antibodies to IL-9 and its receptor can optionally provide complete protection from antigen induced airway hyperresponsiveness and inflammation in mice demonstrating a critical regulatory role for IL-9 in these immune responses. This data demonstrates that although different molecular changes produce biologic variability in airway responsiveness in humans and mice, these changes arise in the same gene(s) (IL-9 and its receptor) that regulate this pathway. Taken together, these observations confirm the critical role of IL-9 and its receptor in airway hyperresponsiveness, asthma and atopic allergy. Moreover, this data demonstrates that agents of the invention, which block IL-9 action(s), protect against an antigen induced response such as those detailed above.

While the role of the IL-9 gene, its receptor and their functions in atopic allergy, asthma and related disorders has been elucidated, a specific need in the art exists for elucidation of the role of genes which are regulated by IL-9 in the etiology of these disorders. Furthermore, most significantly, based on this knowledge, there is a need for the identification of agents that are capable of regulating the activity of these genes, their gene products and their subsequent biological activities for treating these disorders.

SUMMARY OF THE INVENTION

This invention relates to methods of treating atopic allergy and asthma in a mammal comprising administering an effective amount of a 3-aminosteroid compound. In a preferred embodiment, the 3-aminosteroid compound down regulates the IL-9 pathway and asthmatic responses to allergen.

Exemplary 3-aminosteroid compounds used in the methods of the invention include compounds having the chemical formula (I) below:

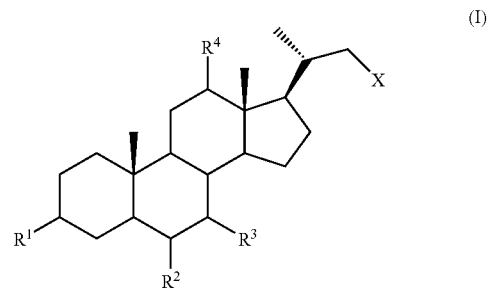

In Formula (I), the X group is selected from the group consisting of —$CH_2$—PO(O$R^5$)$_2$, —NH—$SO_2$—$R^5$, —NH—CO—O$R^5$, —$CH_2$—CO—$NH_2$, —$CH_2$—CO—NH—$R^8$, —$CH_2$—$CO_2$—$R^5$,

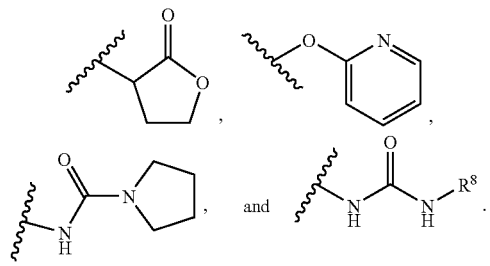

The $R^1$ group is selected from the group consisting of $R^6$—NH—,

The $R^2$, $R^3$, and $R^4$ groups are each independently selected from the group consisting of H, —OH, —OAc, and The $R^5$ group is a $C_{1-12}$ alkyl, and the $R^6$, $R^7$ and $R^8$ are each independently selected from the group consisting of H, $C_{1-6}$ alkyl, and phenyl. The invention also relates to certain novel 3-aminosteroid compounds having the formula (I).

This invention includes a method for identifying a immunomodulatory 3-aminosteroid compound comprising culturing peripheral blood lymphocytes in the presence of a 3-aminosteroid compound and a mitogen to form cell aggregates; and determining the number of cell aggregates wherein an immunomodulatory 3-aminosteroid compound reduces the number of cell aggregates when compared to peripheral blood lymphocytes cultured in the absence of the 3-aminosteroid compound.

In an another embodiment, this invention also encompasses a method for identifying a immunomodulatory 3-aminosteroid compound comprising culturing peripheral blood lymphocytes in the presence of a 3-aminosteroid compound and a mitogen; and determining the level of IL-9 mRNA wherein an immunomodulatory 3-aminosteroid compound reduces the level of IL-9 mRNA when compared to peripheral blood lymphocytes cultured in the absence of the 3-aminosteroid compound. In a preferred embodiment the peripheral blood lymphocytes are cultured in the presence of mitogen for about twelve hours.

In yet another embodiment, the invention includes a method for identifying a immunomodulatory 3-aminosteroid compound comprising culturing peripheral blood lymphocytes isolated from antigen-stimulated mammal in the presence of a 3-aminosteroid compound and an antigen to form cell aggregates; and determining the number of cell aggregates wherein an immunomodulatory 3-aminosteroid compound reduces the number of cell aggregates when compared to peripheral blood lymphocytes cultured in the absence of the 3-aminosteroid compound. In a preferred embodiment, the peripheral blood lymphocytes are cultured in the presence of antigen for three days and the antigen-stimulated mammal is a mouse.

In a further embodiment, the invention includes a method for identifying a immunomodulatory 3-aminosteroid compound comprising culturing cells which proliferate in response to IL-9 in the presence of IL-9 and a 3-aminosteroid compound; and measuring the level of cell proliferation wherein an immunomodulatory 3-aminosteroid compound reduces the level of cell proliferation induced by IL-9 when compared to cells cultured in the absence of the 3-aminosteroid compound. In a preferred embodiment, the cells which proliferate in response to IL-9 are Mo7e cells.

The accompanying figures, which are incorporated in and constitute a part of this specification, illustrate several embodiments of the invention and, together with the description, serve to explain the principle of the invention.

DETAILED DESCRIPTION OF THE INVENTION

Figure 1:
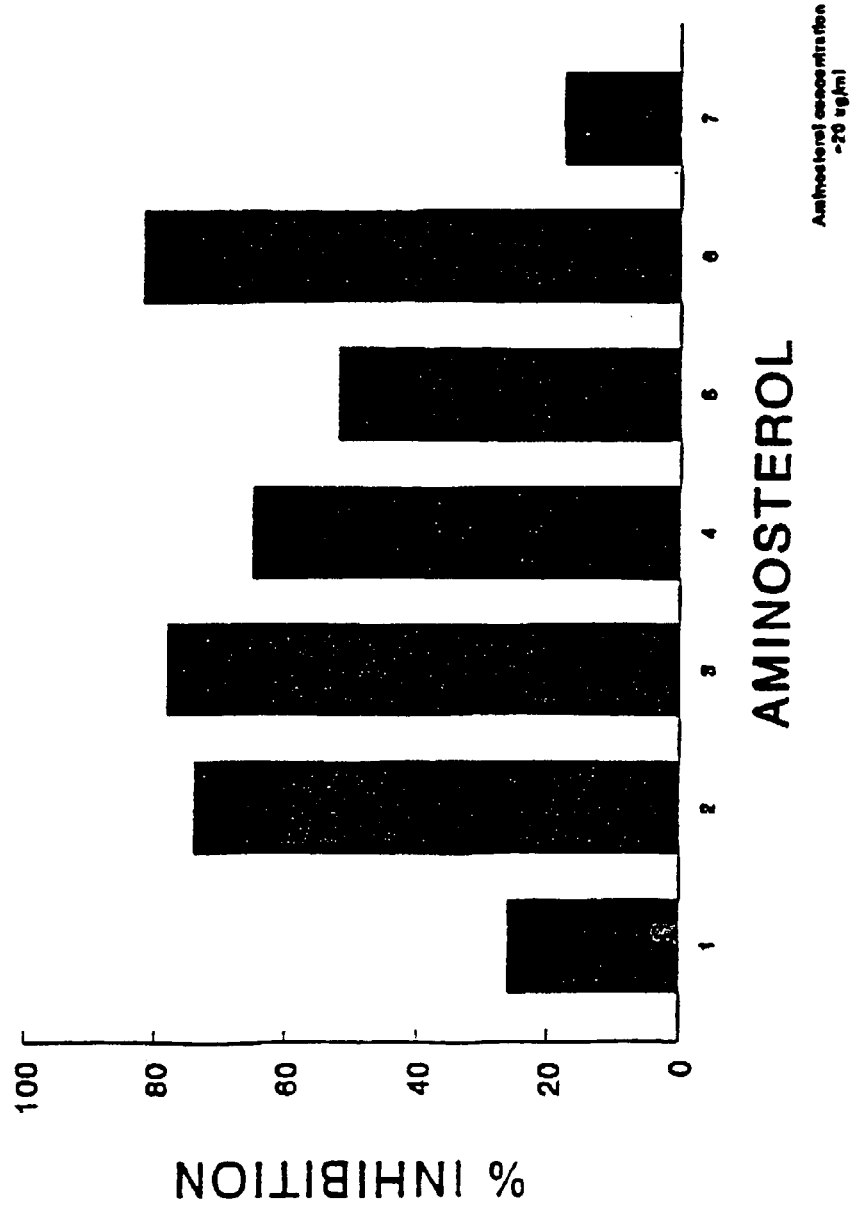
FIG. 1: Inhibition by various 3-aminosteroids of IL-9 mediated M07e proliferation.

Applicant has resolved the needs in the art by elucidating an IL-9 pathway and compositions that affect that pathway that may be used in the diagnosis, prevention or treatment of atopic allergy including asthma and related disorders. Asthma encompasses inflammatory disorders of the airways with reversible airflow obstruction. Atopic allergy refers to atopy and related disorders including asthma, bronchial hyperresponsiveness, rhinitis, urticaria, allergic inflammatory disorders of the bowel and various forms of eczema. Atopy is a hypersensitivity to environmental allergens expressed as the elevation of serum IgE or abnormal skin test responses to allergens as compared to controls.

Further evidence defining the role of IL-9 in the pathogenesis of atopic allergy, bronchial hyperresponsiveness, asthma and related disorders derives directly from the applicants observation that IL-9 is critical to a number of antigen induced responses in mice. When the functions of IL-9 are down-regulated by antibody or 3-aminosteroid, the animals can be completely protected from the antigen induced responses. These responses include: bronchial hyperresponsiveness, eosinophilia and elevated cell counts in bronchial lavage, histologic changes in the lung associated with inflammation and elevated serum IgE. The treatment of such responses, which are critical to the pathogenesis of atopic allergy and which characterize the allergic inflammation associated with asthma, by the down-regulation of the functions of IL-9, are within the scope of this invention.

Applicants have found that 3-aminosteroid compounds are also useful in the inhibition of signal transduction due to IL-9 stimulation. 3-aminosteroid compounds which are useful in this invention are described in U.S. Pat. No. 5,637,691 and related U.S. Pat. Nos. 5,733,899 and 5,721,226 as well as in U.S. Pat. No. 5,840,740 and its related U.S. Pat. Nos. 5,795,885; 5,763,430; 5,840,936; 5,874,597; 05,792,635; 5,994,336 and 5,847,172 which are specifically incorporated herein by reference. In a preferred embodiment of the invention, 3-aminosteroid compounds A, B, D, J and L and derived analogues are useful for the treatment of atopic allergy and asthma. Any compounds derived from compounds A, B, D, J and L including alterations to the core sterol molecule, which are useful for the treatment of atopic allergy and asthma is encompassed in the invention.

Applicant also provides for a method to screen for the compounds that down-regulate the expression of IL-9 or the functions controlled by IL-9. One may determine whether the functions expressed by IL-9 are down-regulated using techniques standard in the art (Miyazawa et al., (1992) Blood 80, 1685–1692; Yin et al., (1994) J. Biol. Chem. 269, 26614–26617; Renauld et al., (1992) Proc. Natl. Acad. Sci. USA 89, 5690–5694; Chang et al., (1994) Blood 83, 3199–3205). In one embodiment, serum IgE may be measured using techniques well known in the art (Meyers et al., (1994) Genomics 23, 464–470) to assess the efficacy of a compound in down-regulating the functions of IL-9 in vivo. In another in vivo assay, bronchial hyperresponsiveness and eosinophilia in bronchoalveolar lavage may be measured using techniques well known in the art (Meyers et al., (1994) Genomics 23, 464–470).

In yet another embodiment, the functions of IL-9 may be assessed in vitro. Specific assays may be based on regulation, in part, of the proliferation of T lymphocytes, IgE synthesis and release from mast cells by IL-9 (Renauld et al., (1990) J. Immunol. 144, 4235–4241; Kelleher et al., (1991) Blood 77, 1436–1441; Houssiau et al., (1995) J. Immunol. 154, 2624–2630; Miyazawa et al., (1992) Blood 80, 1685–1692; Yin et al., (1994) J. Biol. Chem. 269, 26614–26617; Renauld et al., (1992) Proc. Natl. Acad. Sci. USA 89, 5690–5694; Chang et al., (1994) Blood 83, 3199–3205). Another assay involves the ability of human IL-9 to specifically induce the rapid and transient tyrosine phosphorylation of multiple proteins in M07e cells (Miyazawa et al., (1992) Blood 80, 1685–1692). Because this response is dependent on the expression and activation of the IL-9 receptor, it represents a simple method or assay for the characterization of potentially valuable compounds. The tyrosine phosphorylation of Stat3 transcriptional factor appears to be specifically related to the actions of IL-9 (Yin et al., (1994) J. Biol. Chem. 269, 26614–26617) and this response represents a simple method for the characterization of compounds within the invention. Still another method to characterize the function of IL-9 and similar molecules involves the well known murine TS1 clone and the D10 clone available from ATCC which is used to assess human IL-9 function with a cellular proliferation assay (Renauld et al., (1992) Proc. Natl. Acad. Sci. USA 89, 5690–5694). Still another method to monitor the effect of pharmacologic compounds is by measuring IL-9 expression in mitogen-stimulated primary lymphocytes, where the suppression of IL-9 prevents the activation of the lymphocytes.

Exemplary 3-aminosteroid compounds for use in the invention have chemical formula (I), shown below:

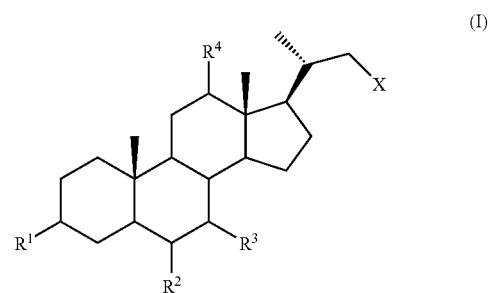

In Formula (I), the X group is selected from the group consisting of $-CH_2-PO(OR^5)_2$, $-NH-SO_2-R^5$, $-NH-CO-OR^5$, $-CH_2-CO-NH_2$, $-CH_2-CO-NH-R^8$, $-CH_2-CO_2-R^5$,

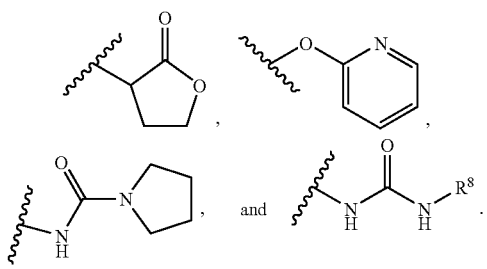

The $R^1$ group is selected from the group consisting of $R^6-NH-$,

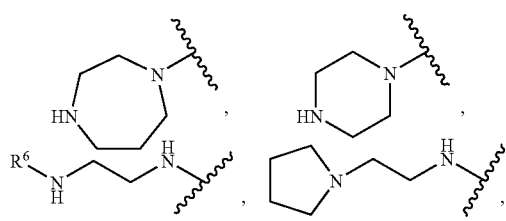

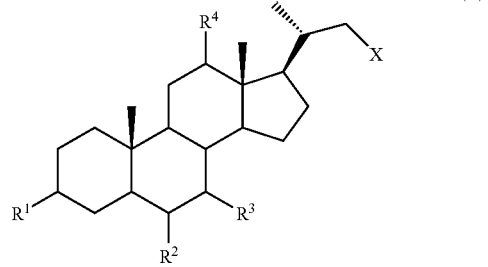

The R⁵ group is a $C_{1-12}$ alkyl, and the $R^6$, $R^7$ and $R^8$ are each independently selected from the group consisting of H, $C_{1-6}$ alkyl, and phenyl.

Exemplary 3-aminosteroid compounds used in the methods of the invention, include the following:

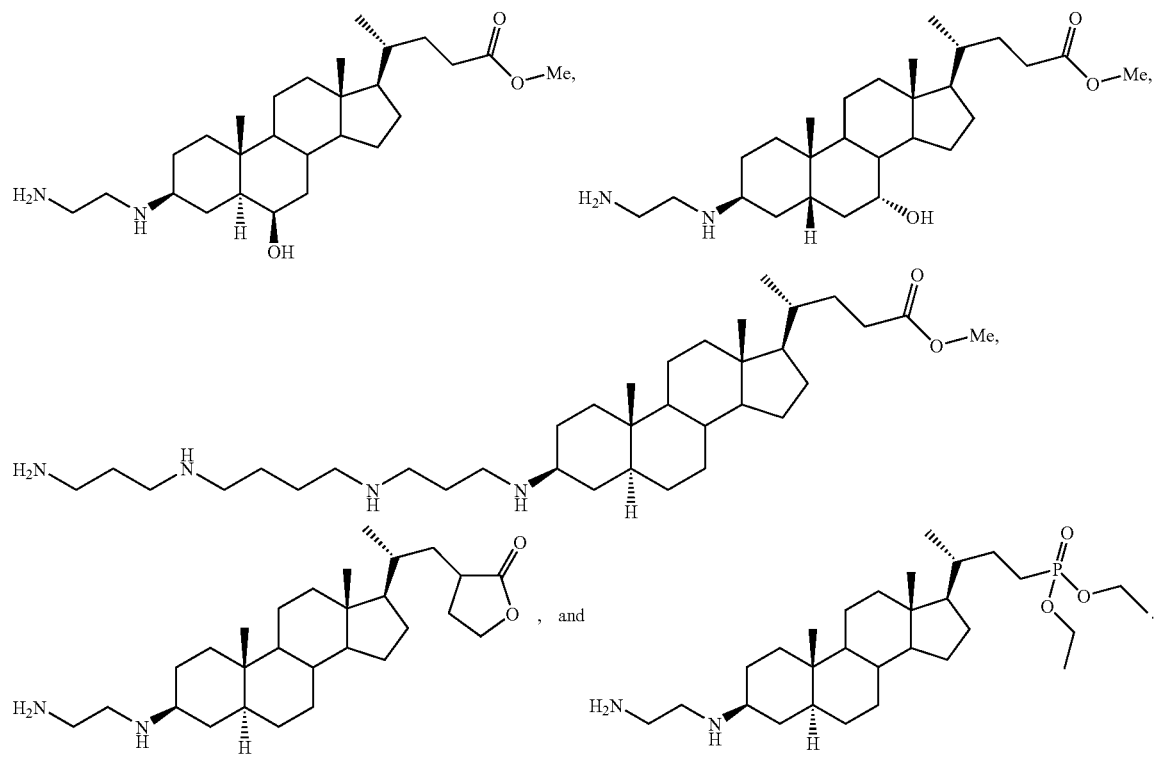

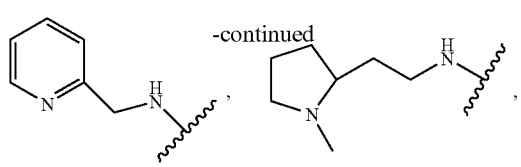

-continued

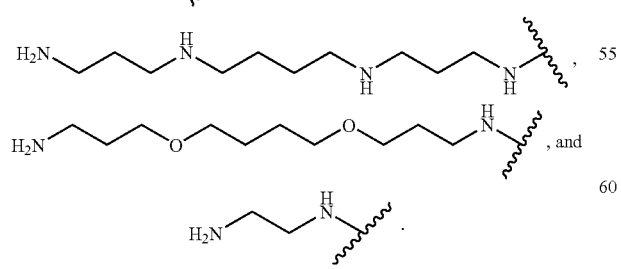

The $R^2$, $R^3$, and $R^4$ groups are each independently selected from the group consisting of H, —OH, —OAc, and In addition, the invention also relates to certain novel 3-aminosteroid compounds of formula (I). Such compounds are also useful in the practice of the methods of the invention. These include compounds of formula (II), below:

The X group is selected from the group consisting of —$CH_2$—$PO(OR^5)_2$, —NH—$SO_2$—$R^5$, —NH—CO—$OR^5$, —$CH_2$—CO—$NH_2$, —$CH_2$—CO—NH—$R^8$, —$CH_2$—$CO_2$—$R^5$,

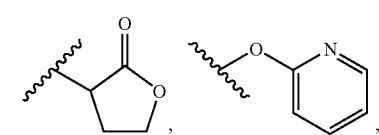

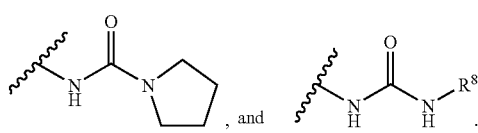

The $R^1$ is selected from the group consisting of $R^6$—$NH_2$—,

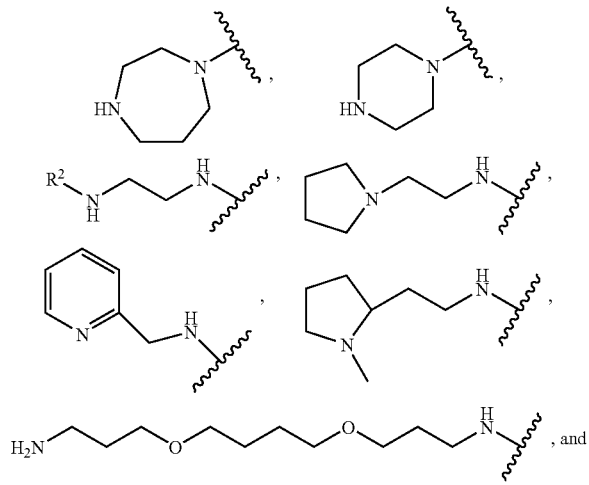

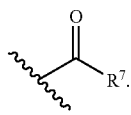

The $R^2$, $R^3$, and $R^4$ groups are each independently selected from the group consisting of H, —OH, —OAc, and

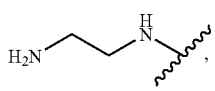

The $R^5$ group is a $C_{1-12}$ alkyl, and the $R^6$, $R^7$ and $R^8$ groups are each independently selected from the group consisting of H, $C_{1-6}$ alkyl, and phenyl.

An embodiment of the invention relates to compounds of formula (II), where the X is selected from the group consisting of —$CH_2$—$PO(OR^5)_2$, —NH—$SO_2$—$R^5$, —NH—CO—$OR^5$, —$CH_2$—CO—$NH_2$, —$CH_2$—CO—NH—$R^8$,

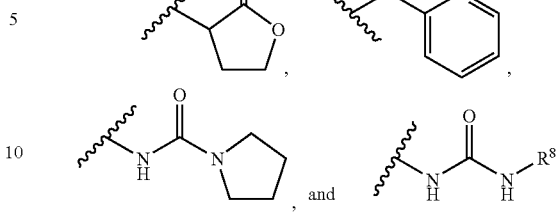

Another embodiment of the invention relates to compounds of formula (II), where the X group is —$H_2CO_2$—$R^5$, and the $R^1$ group is selected from the group consisting of: $R^6$—$NH_2$—,

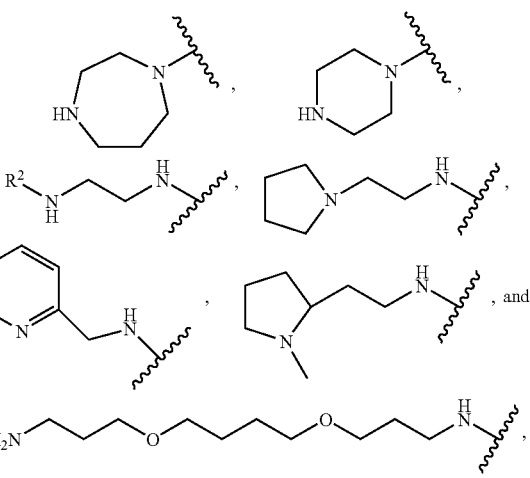

In this embodiment, the $R^2$, $R^3$, and $R^4$ groups are independently selected from the group consisting of H, —OH, —OAc, and

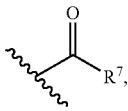

the $R^5$ group is a $C_{1-12}$ alkyl, and the $R^6$ and $R^7$ groups are each independently selected from the group consisting of H, $C_{1-6}$ alkyl, and phenyl.

In yet another emobidmen, the invention also relates to compounds of formula (II), where the X group is —$CH_2$—$CO_2$—$R^5$, the $R^1$ group is

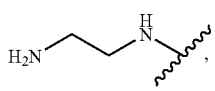

and the $R^2$, $R^3$, and $R^4$ groups are each independently selected from the group consisting of H, —OH, —OAc, and

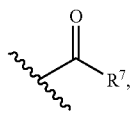

with the proviso that at least one of $R^2$, $R^3$, and $R^4$ is

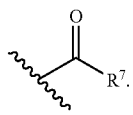

In this embodiment, the $R^5$ group is a $C_{1-12}$ alkyl, and $R^7$ is selected from the group consisting of H, $C_{1-6}$ alkyl, and phenyl.

It is to be understood in the above discussion that the alkyl groups may be straight or branched. The alkyl and phenyl groups may be optionally substituted with halogen, alkoxy, or a water-solubilizing group. A "water-solubilizing group" is a substituent that increases the solubility of a compound in aqueous solution. Exemplary water-solubilizing groups include, but are not limited to, quaternary amine, sulfate, sulfonate, carboxylate, phosphate, phosphonate, polyether, polyhydroxyl, boronate, and amide groups such as —$CONH_2$ and $CONHCH_3$. The water solubilizing groups may also include sulfo, sulfonamido, carbonamido, sulfamoyl, carbamoyl, hydroxyl, and salts thereof.

In addition, the invention includes pharmaceutical compositions comprising the compounds of the invention or their salts together with a pharmaceutically acceptable carrier. Pharmaceutically acceptable carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical carriers are described in *Remington's Pharmaceutical Sciences*, Mack Publishing Company, 1995, specifically incorporated herein by reference.

In another embodiment, a pharmaceutical compound or composition of the invention is provided as a packaged formulation. The packaged formulation may include a pharmaceutical composition of the invention in a container or inhalation device and printed instructions for administration of the composition to a subject or patient exhibiting the symptoms of asthma or allergy. The packaged formulation may also contain instructions for the administration of the composition to a subject or patient in combination with another compound or composition having a known activity against asthma or allergy. In another format, the packaged formulation may contain the pharmaceutical composition with general written material indicating or suggesting the use of the composition and any other compounds or formulations contained therein for treating a patient diagnosed with or exhibiting the symptoms of asthma or allergy.

The compounds used in the method of treatment of this invention may be administered systemically or topically, depending on such considerations as the condition to be treated, need for site-specific treatment, quantity of drug to be administered and similar considerations.

Topical administration may be used. Any common topical formulation such as a solution, suspension, gel, ointment or salve and the like may be employed. Preparation of such topical formulations as are well described in the art of pharmaceutical formulations as exemplified, for example, by *Remington's Pharmaceutical Sciences*. For topical application, these compounds could also be administered as a powder or spray, particularly in aerosol form. The active ingredient may be administered in pharmaceutical compositions adapted for systemic administration. As is known, if a drug is to be administered systemically, it may be confected as a powder, pill, tablets or the like or as a syrup or elixir for oral administration. For intravenous, intra-peritoneal or intra-lesional administration, the compound will be prepared as a solution or suspension capable of being administered by injection. In certain cases, it may be useful to formulate these compounds in suppository form or as an extended release formulation for deposit under the skin or intramuscular injection. In a preferred embodiment, the compounds of this invention may be administered by inhalation. For inhalation therapy the compound may be in a solution useful for administration by metered dose inhalers or in a form suitable for a dry powder inhaler.

An effective amount is that amount which will down-regulate IL-9 activity. A given effective amount will vary from condition to condition and in certain instances may vary with the severity of the condition being treated and the patient's susceptibility to treatment. Accordingly, a given effective amount will be best determined at the time and place through routine experimentation. However, it is anticipated that in the treatment of atopic allergy, asthma and asthma-related disorders in accordance with the present invention, a formulation containing between 0.001 and 5% by weight, preferably about 0.01 to 1%, will usually constitute a therapeutically effective amount. When administered systemically, an amount between 0.01 and 100 mg per kg body weight per day, but preferably about 0.1 to 10 mg/kg, will effect a therapeutic result in most instances.

Other embodiments of the invention will be apparent to those skilled in the art from consideration of the specification and practice of the invention disclosed. It is intended that the specifications and examples be considered exemplary only with a true scope of the invention being indicated by the claims. Having provided this background information, applicant now describes preferred aspects of the invention.

EXAMPLE 1

RNA Isolations, RT-PCR, Cloning and Sequencing of RT-PCR Products

Total cellular RNA was extracted after 24 hours from cultured PBMC, murine spleen cells and M07e cells using RNA PCR corekit (Perkin-Elmer, Foster City Calif.) according to manufacturer's instructions. One microgram of RNA from each source was denatured for five minutes at 65° C. and then reverse transcribed into cDNA using a 20 µl reaction mixture containing 50 units of MLV Reverse Transcriptase, one unit per µl RNAse inhibitor. 2.5 mM oligo d(T)16 primer, 1 mM each dATP, dCTP, dGTP, dTTP, 50 mM KCl, 10 mM Tris-HCl, pH 7.0, 25 mM $MgCl_2$. The reaction mixture was pipetted into thermocycler tubes, placed in a PCR thermal cycler and subjected to one cycle (fifteen minutes at 42° C., five minutes at 99° C. and five minutes at 4° C.). A mock reverse transcription reaction was used as a negative control.

This mixture was then added to a second tube containing 2 mM $MgCl_2$, 50 mM KCl, 10 mM Tris-HCl, pH 7.0, 65.5 µl deionized water, 2.5 units Amplitaq DNA polymerase and 1 µl (20 µM) each of oligonucleotides representing human cDNA IL-9 exon 1 (forward) and exon 5 (reverse), for a final volume of 100 µl. The reaction mixture was subjected to the following PCR conditions: two minutes at 98° C., then 30 cycles at thirty seconds at 94° C., forty seconds at 55° C., forty seconds at 72° C. Finally, the reaction mixture was cycled one time for fifteen minutes at 72° C. for extension.

PCR products representing human IL-9 or IL-9R cDNA were subjected to gel electrophoresis through 1.5% agarose gels and visualized using ethidium bromide staining. Products of a mock reverse transcriptase reaction, in which water was substituted for RNA was used as negative control amplification in all experiments.

EXAMPLE 2

IL-9 Biological Assay in M07e Cells

The M07e line is a human megakaryoblastic cell line, cultured in RPMI-1640, 20% fetal bovine serum and 10 ng/ml IL-3 (R&D Systems). The cell line responds to cytokines including IL-9. The cells were fed and split at $2 \times 10^5$ cells per milliliter every 72 hours.

The cells were centrifuged for ten minutes at 2000 rpm and resuspended in RPMI-1640 with 0.5% bovine serum albumin and insulin-transferrin-selenium (ITS) cofactors (Gibco-BRL). Cells were counted using a hemocytometer and diluted to a concentration of $1 \times 10^5$ cells/ml and plated in a 96-well microtiter plate. Each well contained $2 \times 10^4$ cells per well. The cells were stimulated with 50 ng/ml Stem Cell Factor (SCF) alone, 50 ng/ml SCF plus 50 ng/ml IL-3 (R&D Systems) or 50 ng/ml SCF plus 50 ng/ml IL-9. A control was included which contained cells and basal media only. Serial dilutions of test compounds were added to each test condition in triplicate. Cultures were incubated for 72–96 hours at 37° C. in 5% $CO_2$.

Cell proliferation was assayed using the Abacus® Cell Proliferation Kit (Clontech) which determines the amount of intracellular acid phosphatase present as an indication of cell number. The substrate p-nitrophenyl phosphate (pNPP), was converted by acid phosphatase to p-nitrophenol, which was measured as an indicator of enzyme concentration. pNPP was added to each well and incubated at 37° C. for one hour. Sodium hydroxide was then added to stop the enzymatic reaction and the amount of p-nitrophenol was quantified using a Dynatech® 2000 plate reader at 410 nm wavelength. Standard curves that compare cell number with optical absorbance were used to determine the linear range of the assay. Assay results were only used when absorbance measurements were within the linear range of the assay.

Figure 2:
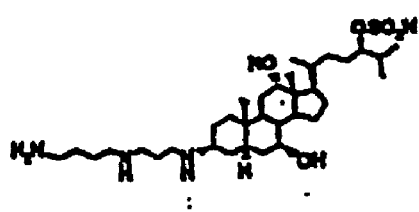
FIG. 2: Aminosterols derived from the dogfish shark.
Figure 2:
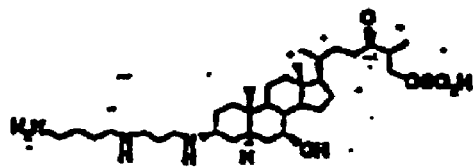
Figure 2:
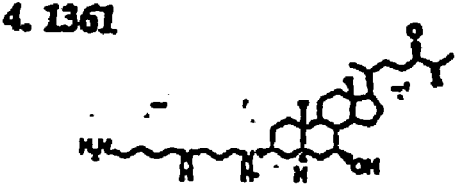

FIG. 1 illustrates the effect of aminosterols isolated from the shark liver (FIG. 2) as set forth in U.S. Pat. Nos. 5,637,691; 5,733,899; 5,721,226 and 5,840,740 incorporated herein by reference, on the IL-9 dependent growth of M07e cells in vitro. Each 3-aminosteroid was incubated with M07e cells at 20 µg/ml of the culture media and inhibition of cellular growth induced by IL-9 was determined by comparison with control conditions (no treatment). There was no evidence for cytotoxicity with any of the treatments. 3-aminosteroids 3 and 6 (FIG. 2) consistently provided the greatest inhibition of growth.

EXAMPLE 3

Identification of Immunomodulatory 3-Aminosteroids In Vitro

Figure 8:
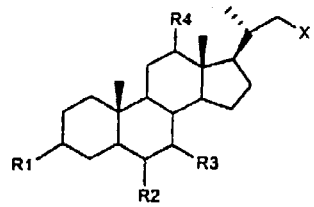
FIG. 8: Novel 3-aminosteroids with ester-isosteres.
Figure 8:
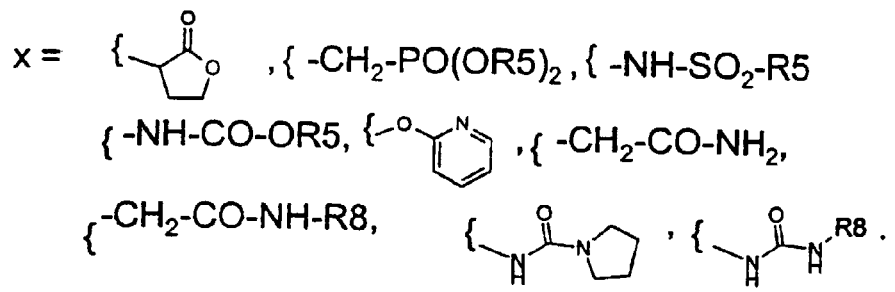
Figure 8:
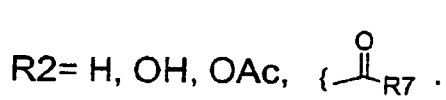
Figure 8:
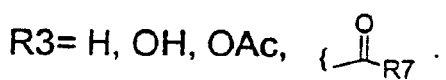
Figure 8:
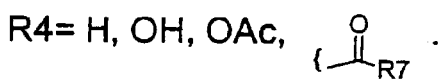
Figure 8:
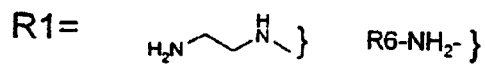
Figure 8:
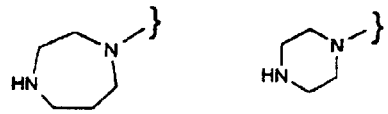
Figure 8:
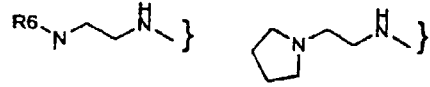
Figure 8:
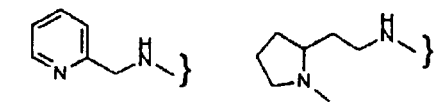
Figure 8:
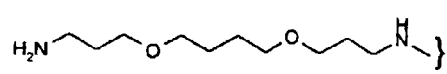
Figure 8:
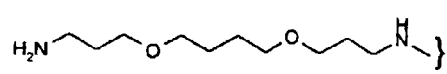
Figure 9:
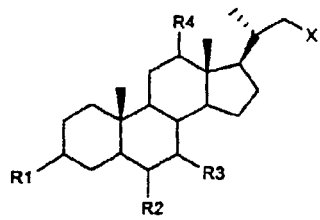
FIG. 9: Novel 3-aminosteroid esters with modified polyamines.
Figure 9:
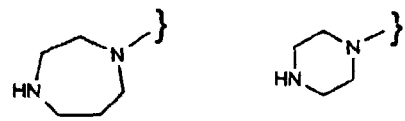
Figure 9:
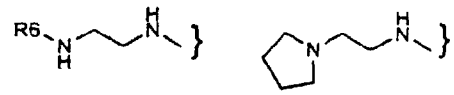
Figure 9:
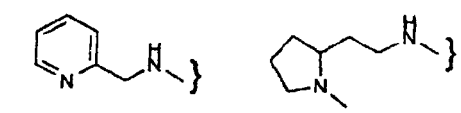
Figure 9:
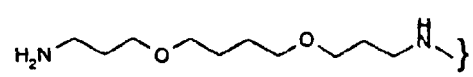
Figure 10:
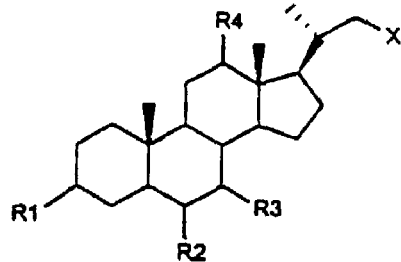
FIG. 10: Novel acylated 3-aminosteroid esters.
Figure 10:
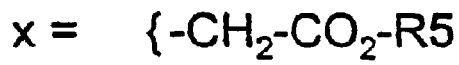
Figure 11:
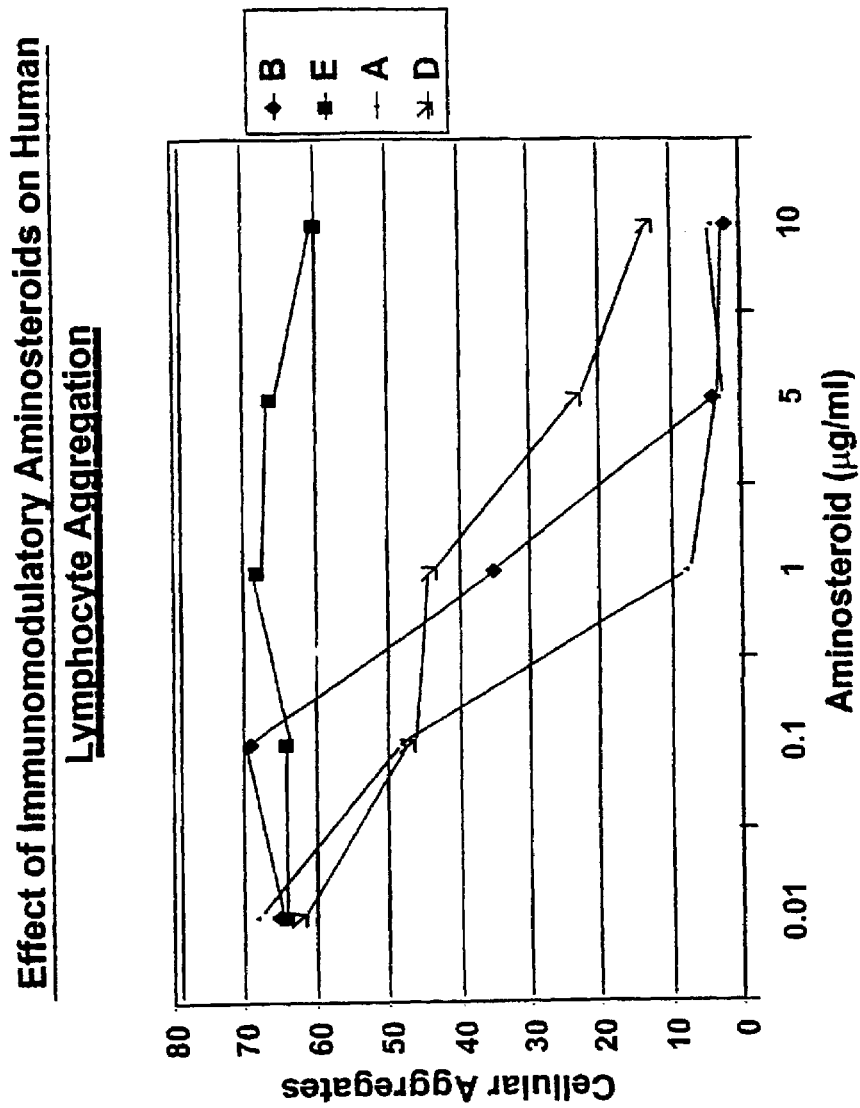
FIG. 11: Effect of 3-aminosteroids on human lymphocyte aggregation.
Figure 12:
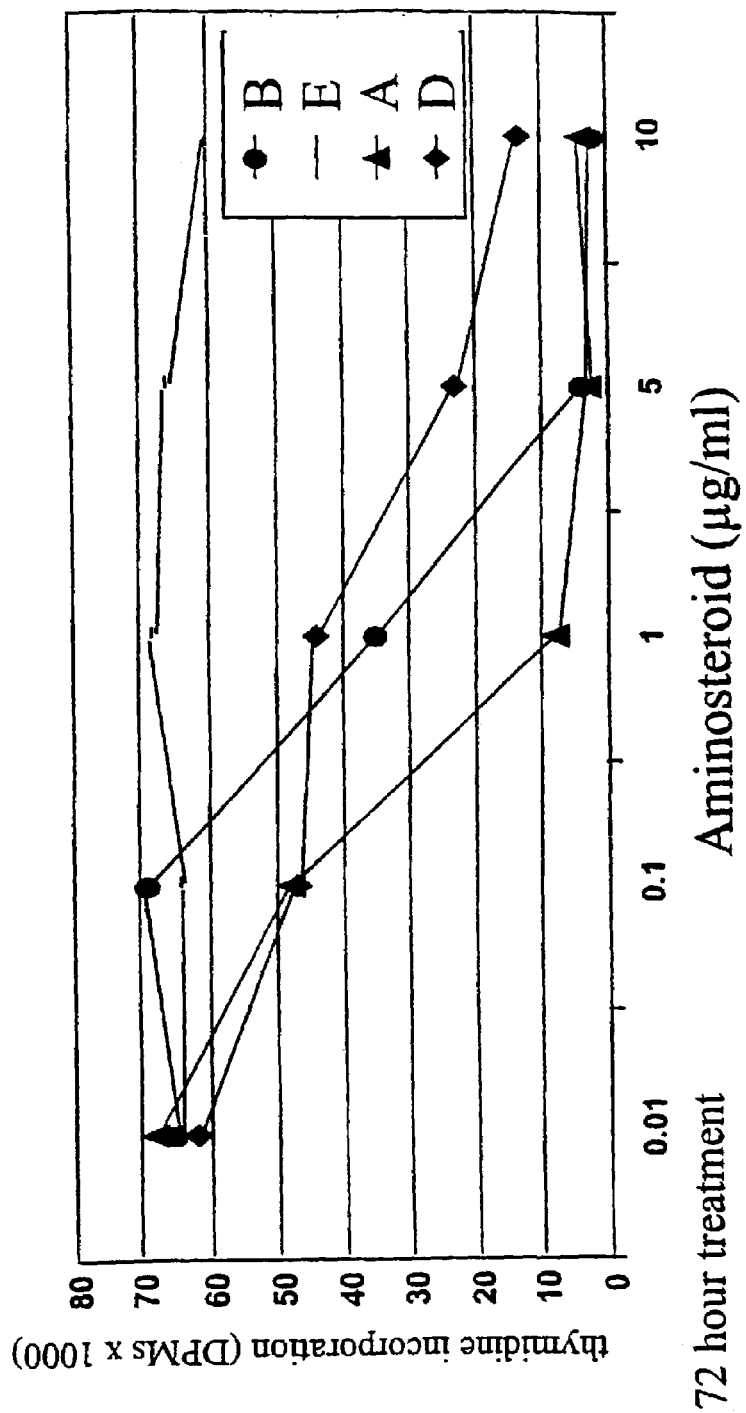
FIG. 12: Effect of 3-aminosteroids on human lymphocyte proliferation.
Figure 13:
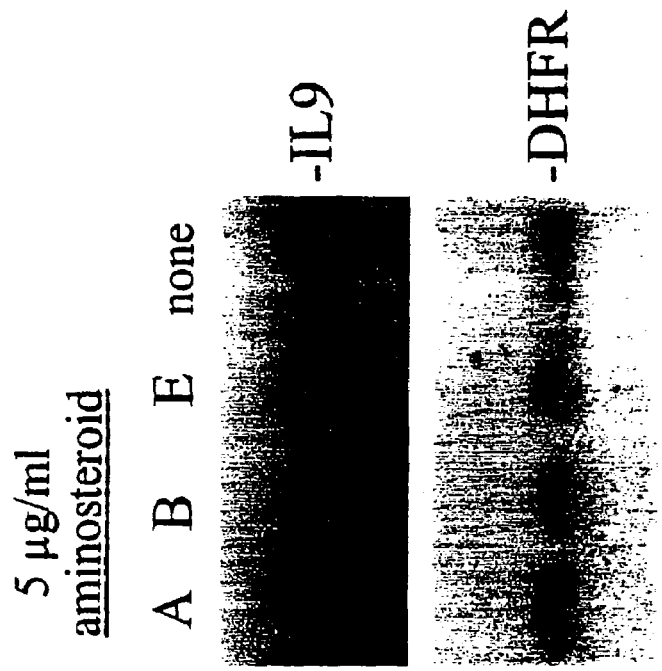
FIG. 13: Effect of 3-aminosteroid on mitogen-induced induction of IL-9

Immunomodulatory 3-aminosteroids (FIGS. 3–7 and Table I) were identified in vitro based on their ability to inhibit homo- or hetero-typic aggregation and subsequent proliferation of mitogen or antigen stimulated murine or human lymphocytes. Human or mouse lymphocytes were isolated from peripheral blood by Ficoll-Hypaque as described (Stoeckert et al., (1990) Exp. Hematol. 18. 1164–1170). For mitogen stimulation, $1 \times 10^5$ cells per well were plated in varying amounts of 3-aminosteroid compounds and assayed for aggregation and proliferation after twelve hours of stimulation by PHA-PMA mitogens. Wells were microscopically counted for aggregates of greater than 100 cells to assess aggregation and proliferation was determined using tritiated thymidine incorporation and analysis on a Packard Top Count as suggested by the manufacture. For antigen stimulation, lymphocytes were isolated from BALBc mice which had been sensitized to *Aspergillus fumigatus* antigen for three weeks and plated at $1 \times 10^5$ cells per well with or without 100 units of *Aspergillus fulmigatus* antigen. Cells were grown for three days and then scored for cellular aggregates and proliferation as described above in the presence or absence of increasing amounts of Compound-B or analogue compounds. Compound-B and Compound-A were able to suppress lymphocyte aggregation (FIG. 11) and proliferation (FIG. 12) at lower doses ($IC_{50}=2.5$ µg/ml & 0.5 µg/ml, respectively) than the highly similar compounds D ($IC_{50}=10$ µg/ml) and E ($IC_{50}>10$ µg/ml). Moreover, the treatment of mitogen-stimulated lymphocytes with compounds A or B was found to block the expression of IL-9 in these cultures in contrast to the effect of control compound E (FIG. 13). Similar results were obtained in assays using antigen mediated response to compounds (not shown). These data demonstrate that both the aggregation and proliferation assays are useful for determining structure-activity relationships for this family of 3-aminosteroids. Table I shows the activity of other 3-aminosteroid compounds in the assays described above. All of the active compounds shown in Table I as well as rational modifications of these compounds as depicted in FIGS. 8–10 are embodiments of the invention

EXAMPLE 4

Efficacy of Immunomodulatory 3-Aminosteroids in Suppression of Asthmatic Response DBA2, C57BL6 or B6D2F1 mice, five to six weeks of age, were obtained from the National Cancer Institute or Jackson Laboratories. Animals were housed in high-efficiency particulate filtered air laminar flow hoods in a virus and antigen free facility and allowed free access to pelleted rodent chow and water for three to seven days prior to experimental manipulation. The animal facilities were maintained at 22° C. and the light:dark cycle is automatically controlled (10:14 hour cycle).

Phenotyping and efficacy of pretreatment. Animals either received no pretreatment or were sensitized by nasal aspiration of *Aspergillus fumigatus* antigen to assess the effect on bronchial hyperresponsiveness, bronchoalveolar lavage and serum IgE. Mice were challenged with Aspergillus or saline intranasally (Monday, Wednesday and Friday for three weeks) and phenotyped twenty-four hours after the last dose. The effect of pretreatment by aminosteroids was used to assess the effect of down-regulating the IL-9 pathway in mice. To determine the bronchoconstrictor response, respiratory system pressure was measured at the trachea and recorded before and during exposure to the drug. Mice were anesthetized and instrumented as previously described. (Kleeberger et al., (1990) Am. J. Physiol. 258, L313–320; Levitt et al., (1995) Clin. Exp. Allergy 25, 61–63; Ewart et al., (1995) J. Appl. Physiol. 79, 560–566). Airway responsiveness was measured to one or more of the following: 5-hydroxytryptamine, acetylcholine, atracurium or a substance-P analogue. A simple and repeatable measure of the change in peak inspiratory pressure following bronchoconstrictor challenge was used which has been termed the Airway Pressure Time Index (APTI). The APTI was assessed by the change in peak respiratory pressure integrated from the time of injection until the peak pressure returns to baseline or plateau. The APTI was comparable to airway resistance, however, the APTI includes an additional component related to the recovery from bronchoconstriction.

Prior to sacrifice, whole blood was collected for serum Ig measurements by needle puncture of the inferior vena cava in anesthetized animals. Samples were centrifuged to separate cells and serum was collected and used to measure total $IgG_1$, $IgG_{2a}$ and IgE levels. Samples not measured immediately were frozen at −20° C.

Serum Igs were measured using an ELISA antibody-sandwich assay. Microtiter plates were coated, 50 µl per well, with rat anti-murine $IgG_1$, $IgG_{2a}$ or IgE antibody (Southern Biotechnology and PharMingen) at a concentration of 2.5 µg/ml in coating buffer of sodium carbonate-sodium bicarbonate with sodium azide. Plates were covered with plastic wrap and incubated at 4° C. for sixteen hours. The plates were washed three times with a wash buffer of 0.05% Tween-20 in phosphate-buffered saline, incubating for five minutes for each wash. Blocking of nonspecific binding sites was accomplished by adding 200 µl per well 5% bovine serum albumin in phosphate-buffered saline, covering with plastic wrap and incubating for two hours at 37° C. After washing three times with wash buffer, duplicate 50 µll test samples were added to the wells. Test samples were assayed after being diluted 1:10, 1:50 and 1:100 with 5% bovine serum albumin in wash buffer. In addition to the test samples, a set of Ig standards (PharMingen) at various liner concentrations in 5% bovine serum albumin in wash buffer, were assayed to generate a standard curve. A blank of no sample or standard was used to zero the plate reader (background). After adding samples and standards, the plate was covered with plastic wrap and incubated for two hours at room temperature. After washing three times with wash buffer, 50 µl of secondary antibody rat anti-murine $IgG_1$, $IgG_{2a}$ or IgE-horseradish peroxidase conjugate was added at a concentration of 250 ng/ml in 5% bovine serum albumin in wash buffer. The plate was covered with plastic wrap and incubated two hours at room temperature. After washing three times with wash buffer, 100 µl of the substrate 0.5 mg/ml o-phenylenediamine in 0.1 M citrate buffer was added to every well. After five to ten minutes the reaction was stopped with 50 µl of 12.5% sulfuric acid and absorbance was measured at 490 nm on a Dynatech® MR5000 plate reader. A standard curve was constructed from the standards with antigen concentration on the x axis (log scale) and absorbance on the y axis (linear scale). The concentration of $IgG_1$, $IgG_{2a}$ or IgE in the samples was interpolated from the standard curve.

Bronchoalveolar lavage and cellular analysis were preformed as previously described (Kleeberger et al., (1990) Am. J. Physiol. 258, L313–320). Lung histology was carried out after the lungs were removed under anesthesia. Since prior instrumentation may introduce artifact, separate animals were used for these studies. Thus, a small group of animals was treated in parallel exactly the same as the cohort undergoing various pretreatments except these animals were not used for other tests aside from bronchial responsiveness testing. After bronchial responsiveness testing, the lungs were removed and submersed in liquid nitrogen. Cryosectioning and histologic examination was carried out in a manner obvious to those skilled in the art.

Figure 14:
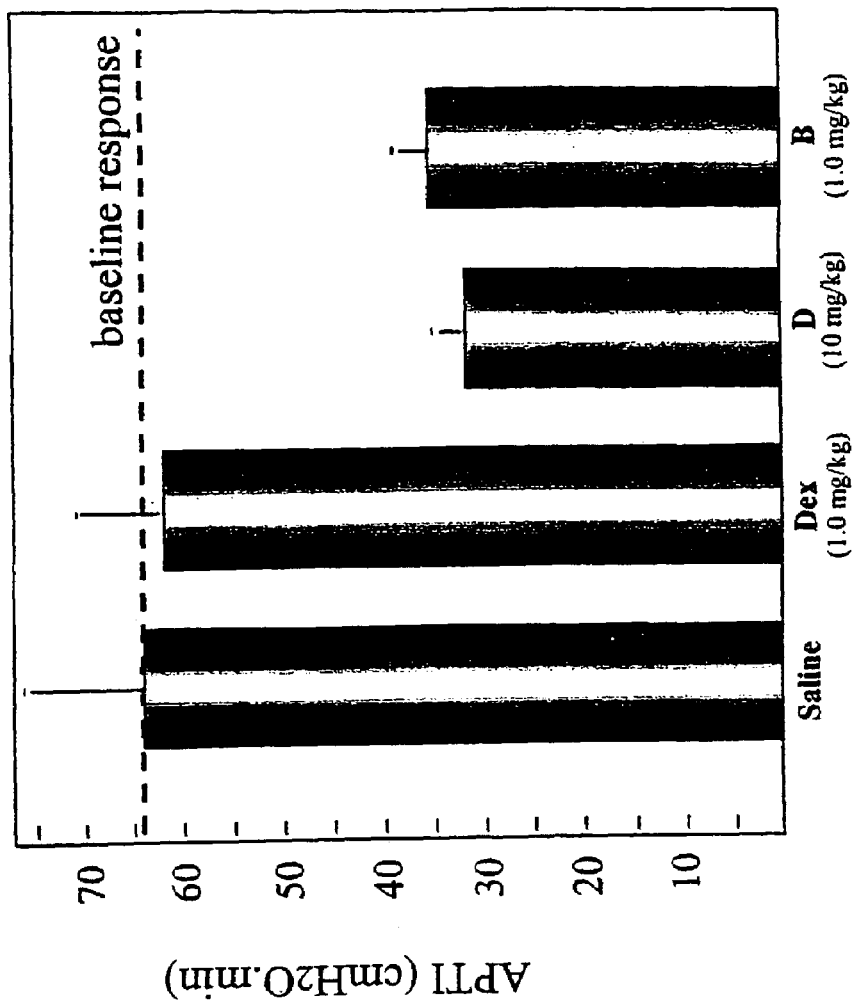
FIG. 14: Inhibition of bronchial hyperresponsiveness in mice by 3-aminosteroids.
Figure 15:
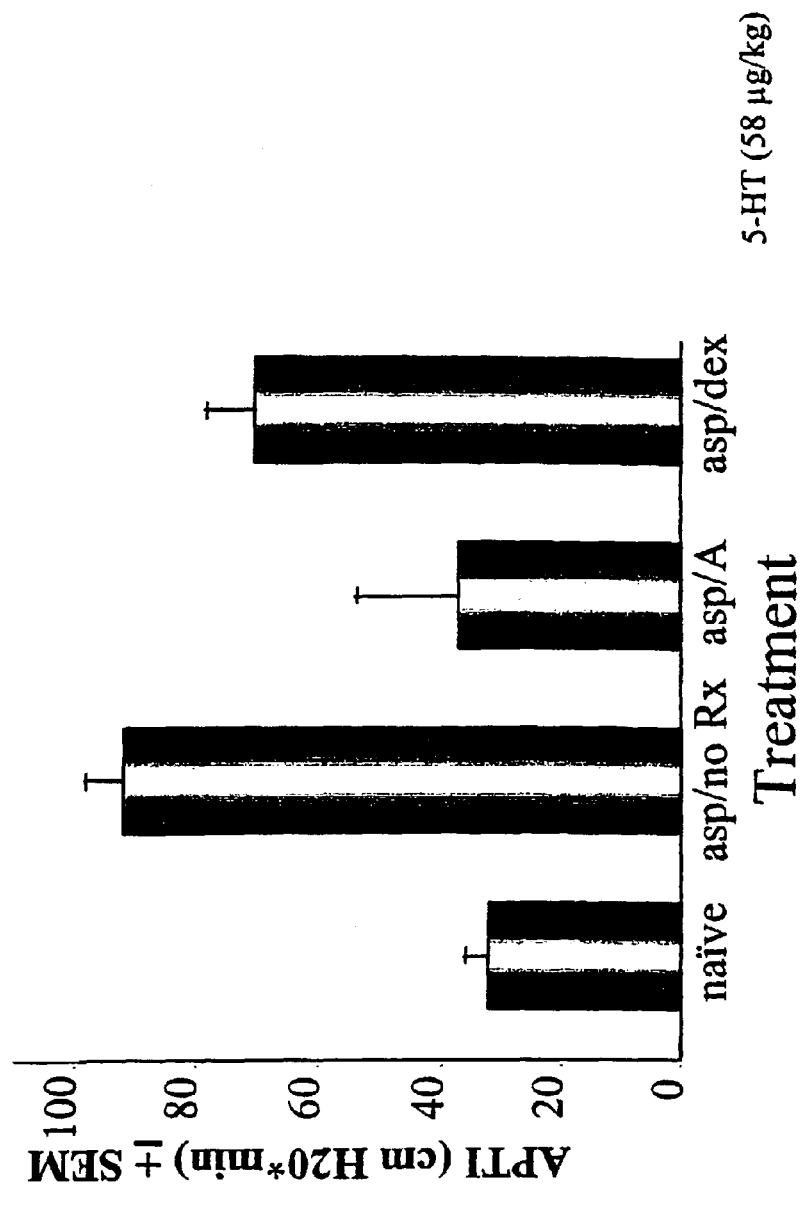
FIG. 15: Inhibition of bronchial hyperresponsiveness in DBA2J mice by dexamethasone and Compound-A.
Figure 16:
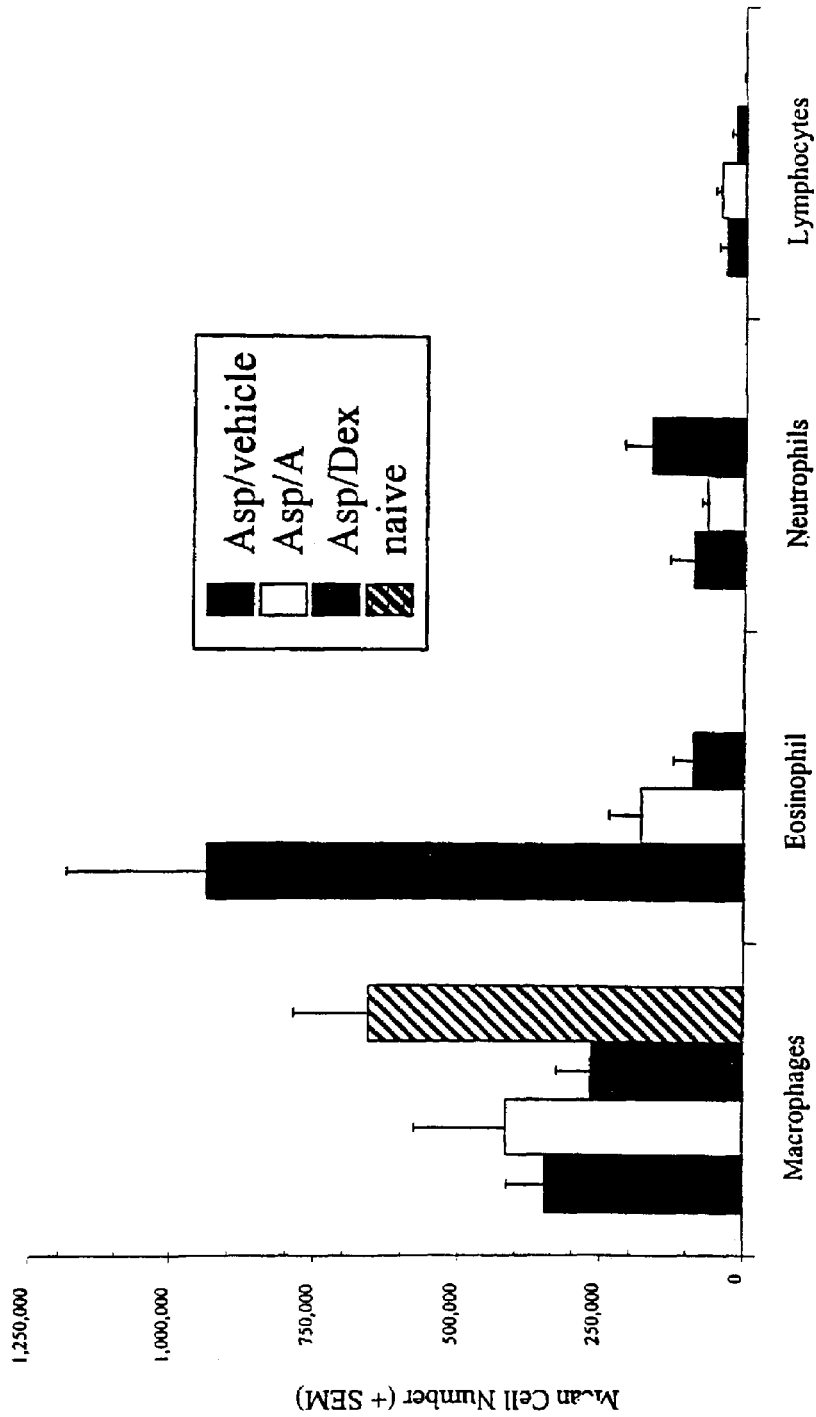
FIG. 16: Inhibition of eosinophilia in mice by dexamethasone and Compound-A.
Figure 17:
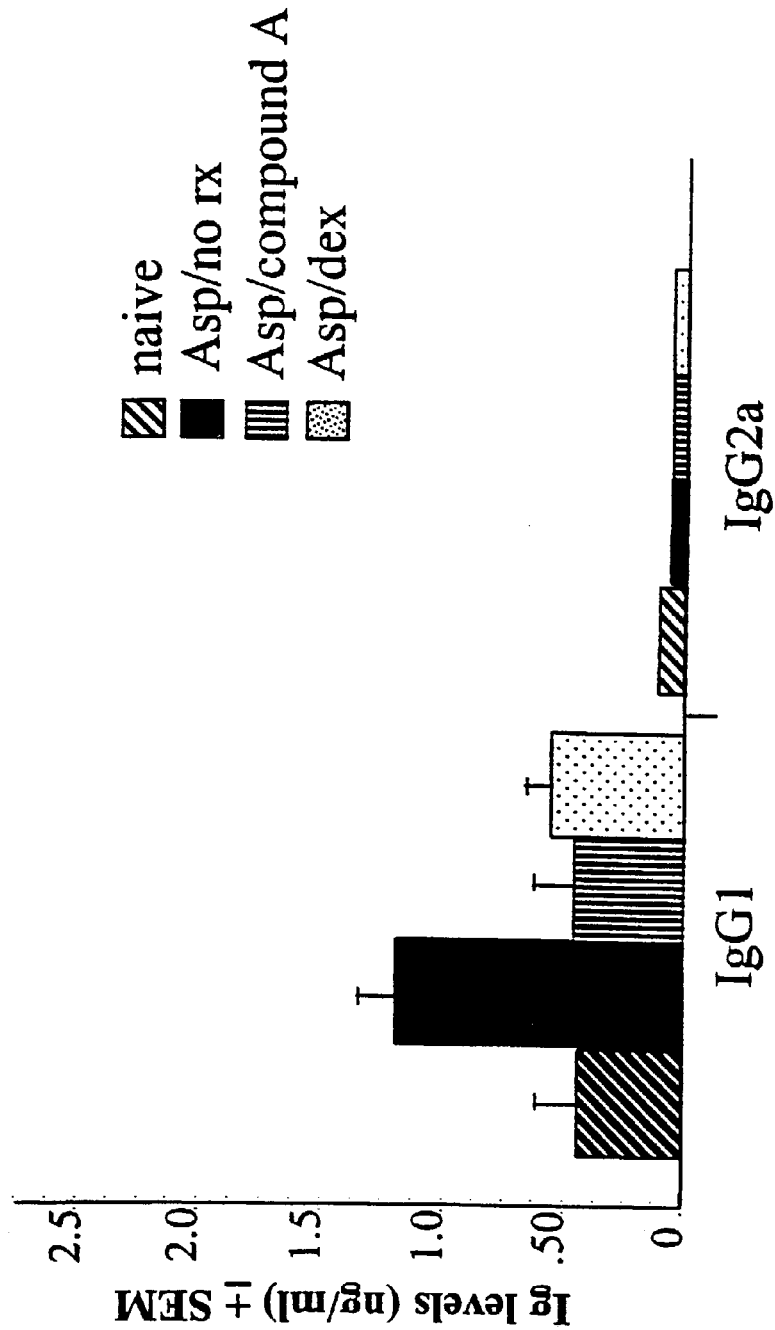
FIG. 17: Inhibition of IgG1 production in sensitized DBA2J mice by dexamethasone and Compound-A.
Figure 18:
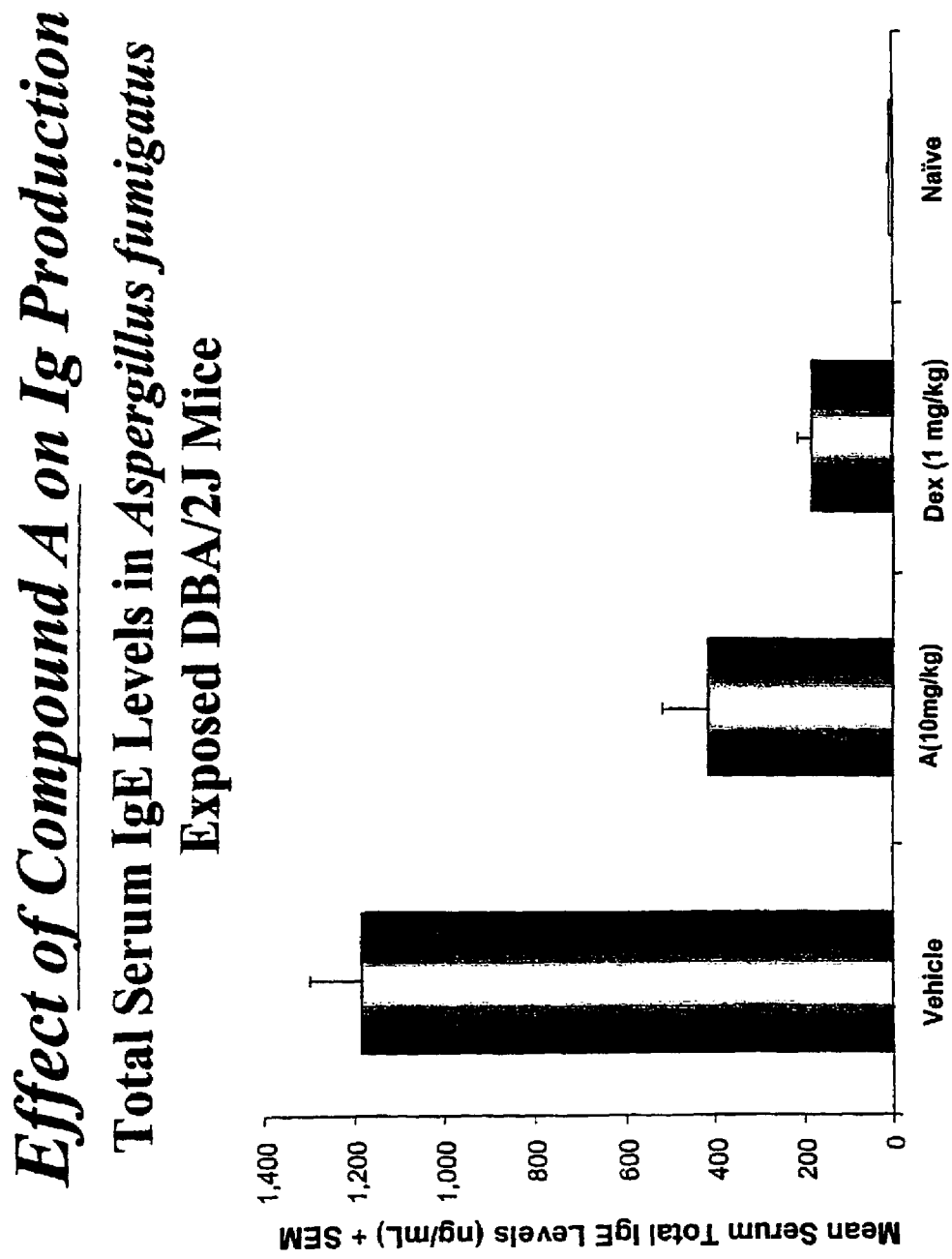
FIG. 18: Inhibition of IgE production in sensitized DBA2J mice by dexamethasone and Compound-A.
Figure 19:
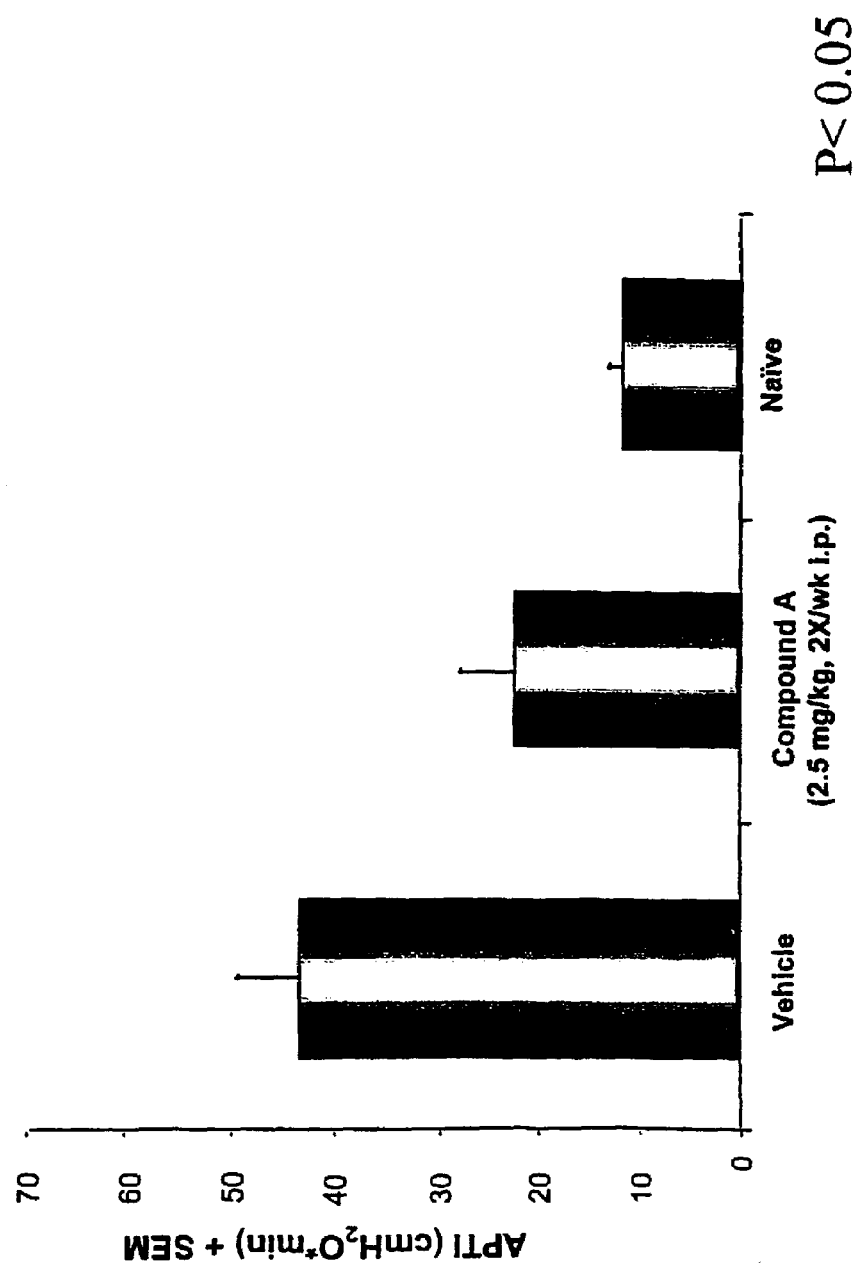
FIG. 19: Inhibition of bronchial hyperresponsiveness in BALBc mice by Compound-A.

Active compounds identified in vitro were tested in vivo for their ability to suppress airway hyperresponsiveness, lung eosinophilia and serum Ig levels using assays described above. Animals were either unsensitized or sensitized to antigen and dosed with a 3-aminosteroid compound ip at either 1 or 10 mg/kg/day for up to three weeks or 2.5 mg/kg twice a week for four weeks. The ability of these compounds to suppress asthmatic type responses is demonstrated by the data in FIGS. 14–19. FIG. 14 demonstrates that both Compounds-B and-D are effective in suppressing bronchial hyperresponsiveness in D2 naive mice, which are hyperresponsive due to elevated IL-9 levels in their lungs (Nicolaides et al., (1997) Proc. Natl. Acad. Sci. USA 94, 13175–13180) and Compound-B is effective at a lower dose than Compound-D. FIG. 15 indicates that the 3-aminosteroid Compound-A is able to block airway hyperresponsiveness in mice sensitized to antigen and that it was more efficacious than the commonly used corticosteroid, dexamethasone (Dex). FIG. 16 demonstrates that eosinophils were the particular cell type affected by Compound-A, suggesting that this compound acts on cell types associated with a TH2-allergic response. The inhibition of a TH2-allergic response was also indicated in FIGS. 17 and 18 where total serum IgG1 and IgE was suppressed but not the TH1 associated immunoglobulin IgG2a FIG. 19 indicates that the 3-aminosteroid Compound-A is able to block airway hyper-responsiveness at a dose as low as 2.5 mg/kg administered twice per week. In summary, these data suggest that 3-aminosteroid compounds and derived analogues have the potential to inhibit asthmatic responses at very low drug concentrations and therefore will be useful for the treatment of asthma with a low incident of side effects in human patients.

EXAMPLE 5

Mechanism of Action In Vivo of Immunomodulatory 3-Aminosteroids

Figure 20:
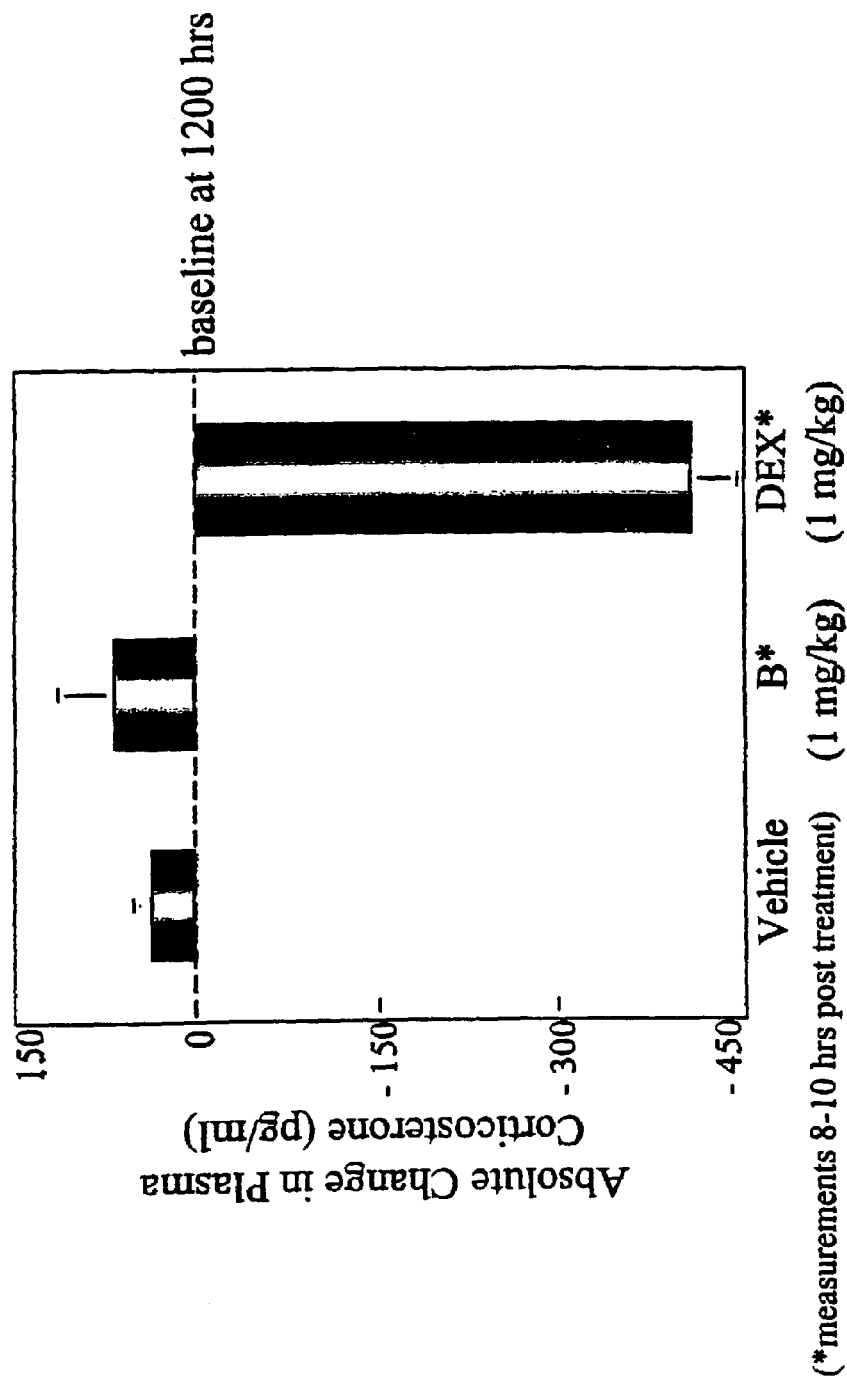
FIG. 20: Effect of dexamethasone or Compound-B on plasma corticosterone in Sprague-Dawley rats.
Figure 21:
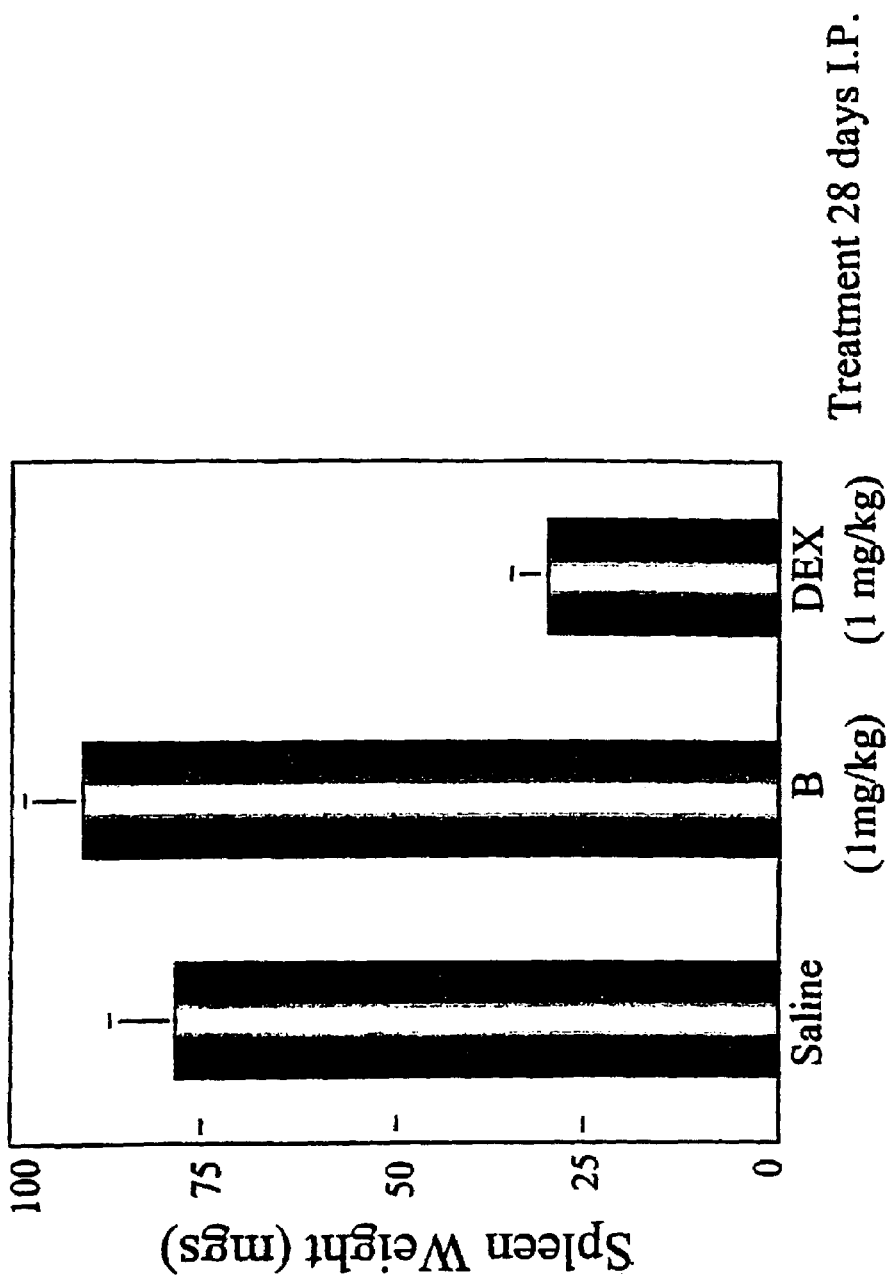
FIG. 21: Effect of dexamethasone or Compound-B on spleen weight in Sprague-Dawley rats.
Figure 22:
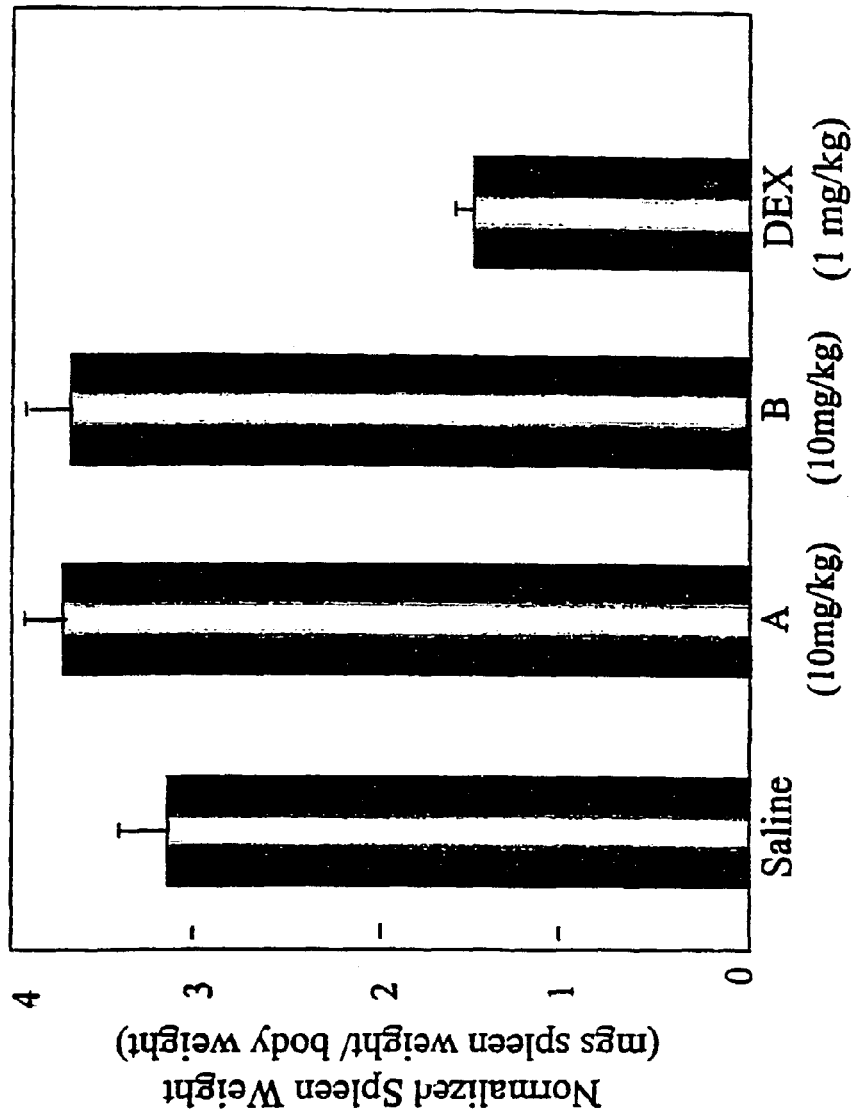
FIG. 22: Effect of Compounds A, B or Dexanethasone on spleen weight in mice.

To determine the mechanism by which 3-aminosteroid compounds function to suppress the asthmatic response to allergen, comparative physiologic assays were carried out utilizing the extensively studied Sprague-Dawley rat model (Scaccianoce et al., (1995) Neuroendocrinology 62, 32–38; Hatzinger et al., (1996) Neuroendocrinology 64, 349–356). Animals were administered 1 mg/kg/day of either the corticosteroid Dexamethasone or Compound-B and analyzed at ten hours for corticosterone and ACTH. As shown in FIG. 20, dexamethasone significantly suppressed absolute levels of plasma corticosterone (>450 fold) eight to ten hours after treatment while Compound-B had no significant effect. Similar results were found for ACTH levels (>100 fold) supporting the finding that Compound-B is acting by a different mechanism from dexamethasone. Longer studies, where drug was administered for 28 days, demonstrated that animals tolerated the 3-aminosteroid compounds better than dexamethasone where weight loss and splenic atrophy were observed (FIG. 21). Similar data was obtained in mice treated with effective doses of either Compounds A or B (10 mg/kg per day for 22 days) where no splenic atrophy was observed in contrast to dexamethasone treatment (FIG. 22). This data combined with the data from Examples 2, 3 and 4 demonstrates that 3-aminosteroid compounds are novel anti-inflammatory and anti-asthma compounds which appear to function by a mechanism unlike that of the dexamethasone class of steroids to suppress the biological response to allergen sensitization.

EXAMPLE 6

3-Aminosteroidal Esters

Figure 3:
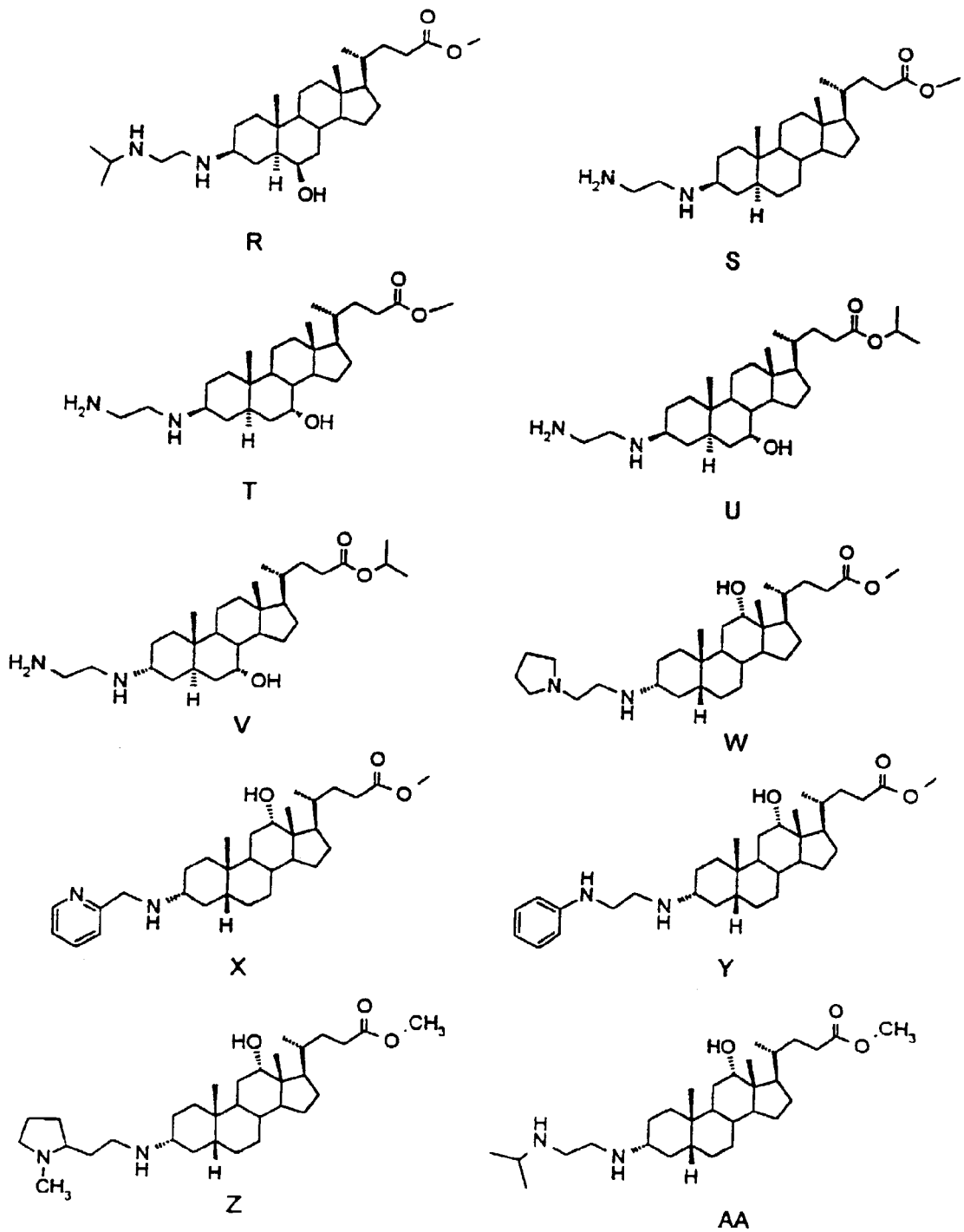
FIG. 3: Analogues of 3-aminosteroids derived from the dogfish shark.
Figure 3:
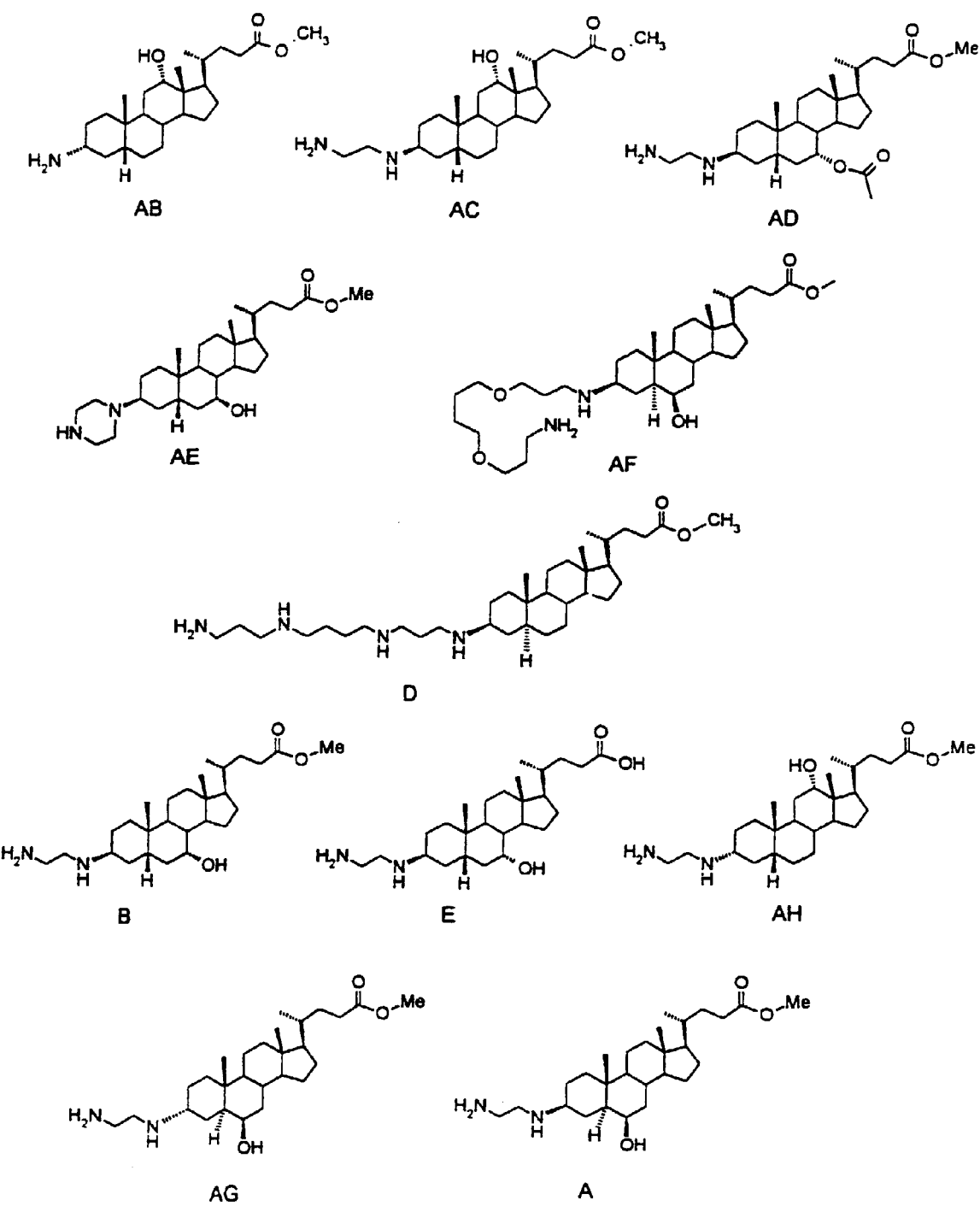
Figure 4:
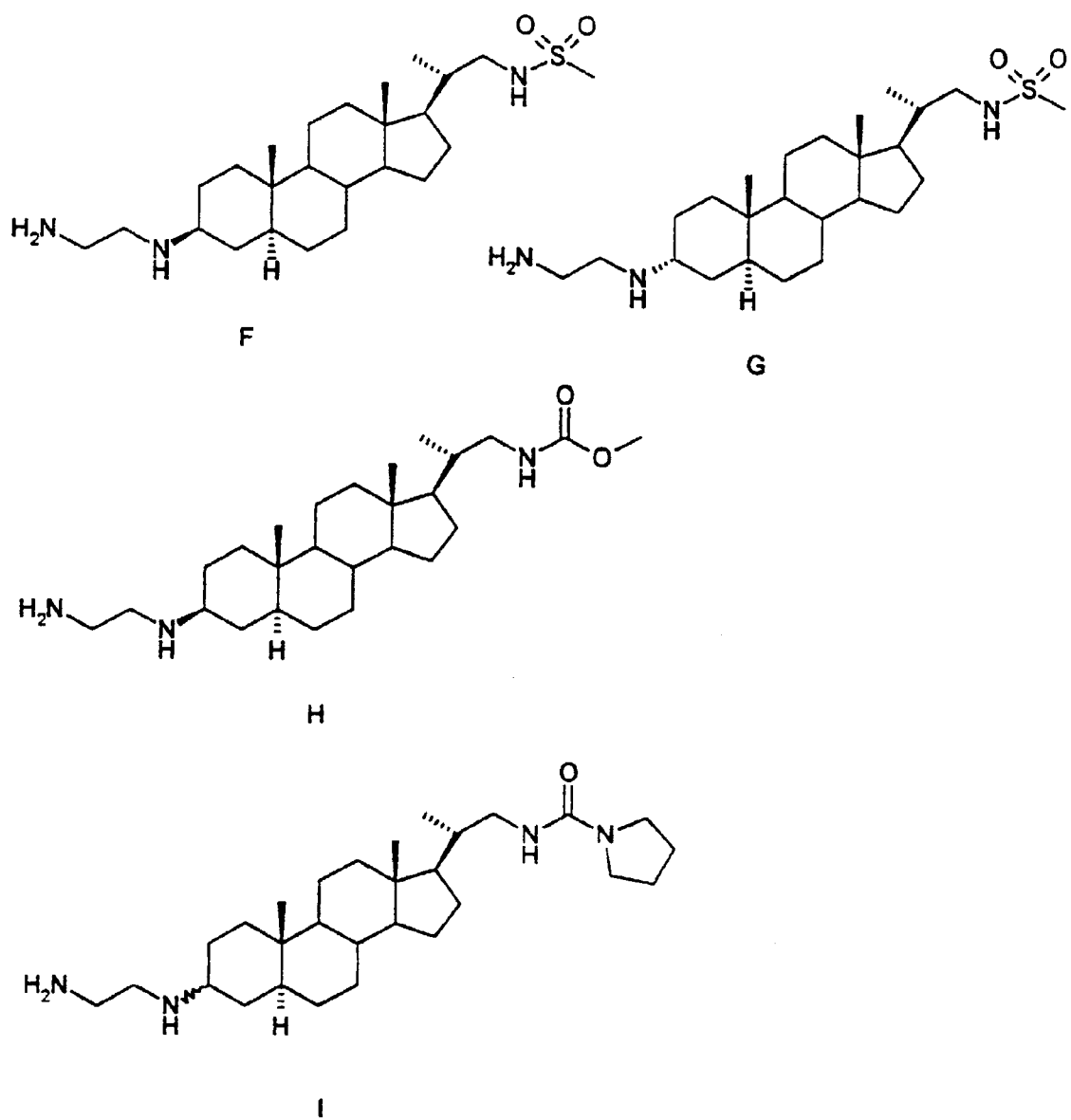
FIG. 4: 3-aminosteroids prepared from acylated or sulfonylated 22-amines.

The majority of the analogues prepared were accessible from the methods described previously (Jones et al., (1996) Steroids 61, 565–571) using the appropriate polyamine and steroidal ester (FIG. 3). In addition, general methods for preparing 3-aminosteroids have also been described previously (Zasloff et al., (1999) U.S. Pat. No. 5,856,535) this reference herein incorporated by reference in its entirety.

A number of 3-aminosteroid analogues were prepared via acylation or sulfonylation of the C22-amine 5, which was prepared as outlined below. The preparation of compounds 1 and 2 has been described previously (Rao et al., (1997) J. Org. Chem. 62, 4541–4545).

Analogues Prepared via Acylation or Sulfonylation of 22-Amine

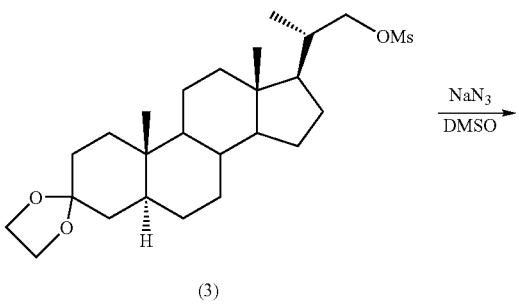

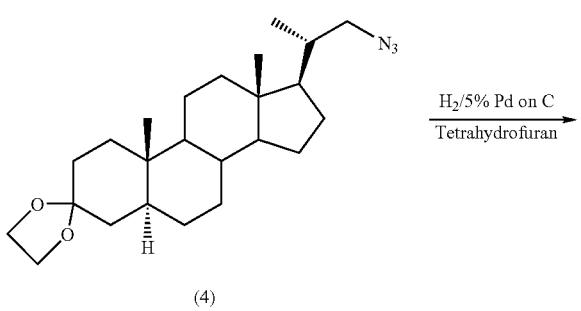

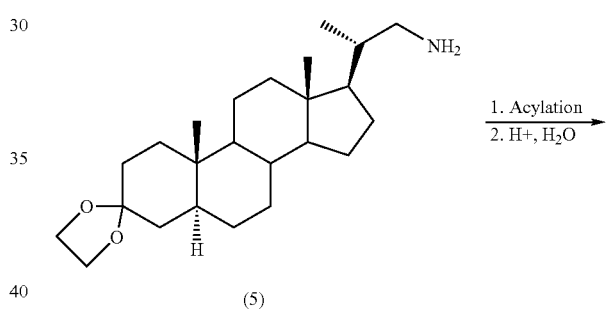

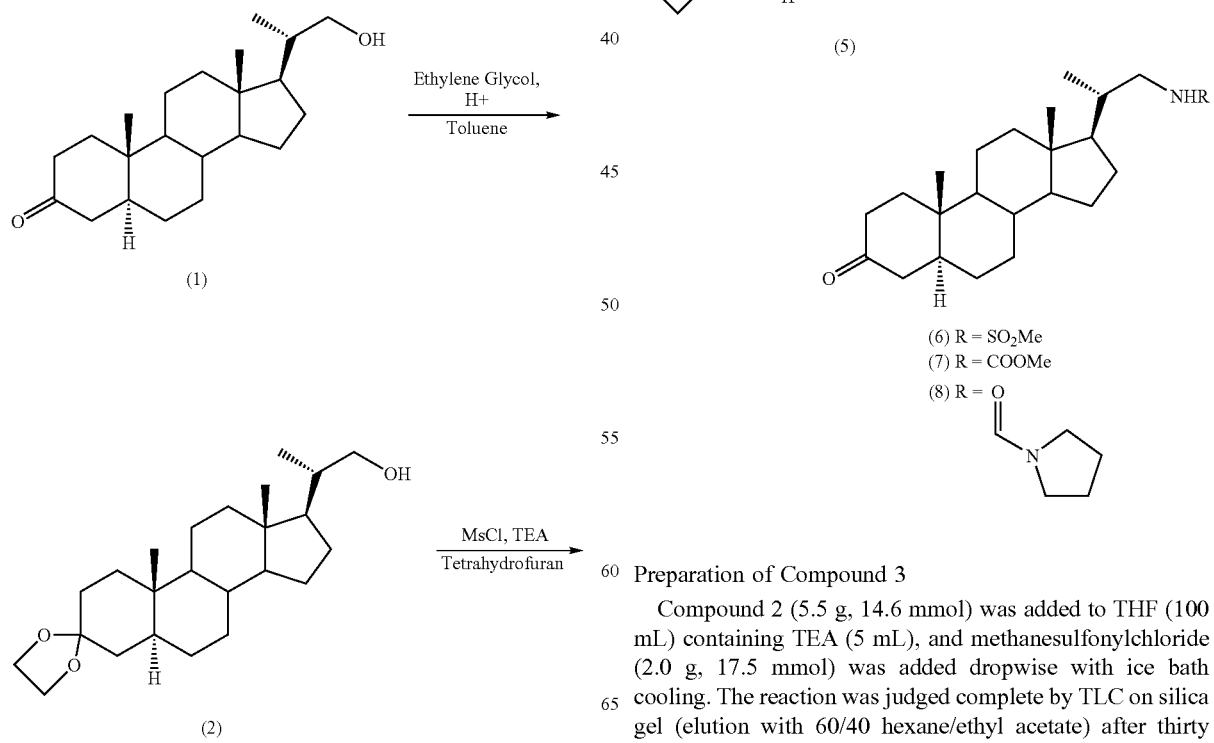

Preparation of Compound 3

Compound 2 (5.5 g, 14.6 mmol) was added to THF (100 mL) containing TEA (5 mL), and methanesulfonylchloride (2.0 g, 17.5 mmol) was added dropwise with ice bath cooling. The reaction was judged complete by TLC on silica gel (elution with 60/40 hexane/ethyl acetate) after thirty minutes. The reaction mixture was worked-up by addition of toluene (100 mL) and saturated sodium bicarbonate. The organic layer was washed alternately with sodium bicarbonate and 0.1 M HCl solution. The pooled organic layers were then dried over sodium sulfate to afford crude compound 3 as an off white solid (5.4 g, 11.9 mmol, 81%). The crude mesylate (3) was carried on without further purification.

Preparation of Compound 4

The crude mesylate (5.0 g, 11.0 mmol) was added to DMSO (150 mL). Sodium azide (2.5 g, 38.5 mmol) was added and the reaction was warmed to 60° C. until judged complete by TLC on silica gel (approximately four hours). The reaction was worked-up by the addition of hexane/ethyl acetate 50/50 (~200 mL). The organic layer was repeatedly washed with water to remove the DMSO. The organic layer was dried over sodium sulfate and the solvent removed in vacuo to give the crude azide 4 (4.2 g, 10.4 mmol, 94%) which was carried on without further purification.

Preparation of Compound 5

The crude azide 4 (4.2 g, 10.4 mmol) was dissolved in THF (100 mL) in a 250 mL Parr flask. The catalyst (400 mg, 5% Pd on carbon) was added wet under a stream of $N_2$. The flask was purged with $N_2$ before introduction of $H_2$ at 50 psi. The reaction was hydrogenated at room temperature for eight hours. The reaction was worked-up by filtration through Celite® to give the C22-amine 5 (3.9 g, 10.3 mmol, 99%), which was of satisfactory purity.

General Procedure for Acylation of Compound 5

The acylations were carried out via a similar procedure. Compound 5 (~500 mg) was dissolved in THF (10 mL) and TEA (2 mL) was added. The flask was chilled in an ice water bath, and the acylating agent (approximately two equivalents) was added dropwise. The reaction was followed by TLC on silica gel (elution with 20/1 chloroform/methanol). The acylating agents used were methanesulfonyl chloride, methyl chloroformate and pyrolidinecarbonyl chloride. After the reactions were judged to be complete, 20% TFA in water (20 mL) was added to the flask. If precipitation occurred, acetone was added until the sterol redissolved. The acid solutions were stirred for approximately two hours before being worked-up by extracting into 50/50 toluene/ethyl acetate. The organic layer was washed with water and saturated sodium bicarbonate, dried over sodium sulfate, and evaporated in vacuo. This provided crude 3-oxo-22-sulfonamide (compound 6, 437 mg, 1.1 mmole, 73%), carbamate (compound 7, 477 mg, 1.2 mmole, 81%) and urea (compound 8, 544 mg, 1.3 mmole, 86%) derivatives of satisfactory purity.

EXAMPLE 7

3-Aminosteroids Prepared from Acylated or Sulfonylated 22-Amines

Compounds F, G, H and I (FIG. 4) were prepared from acylated or sulfonylated 22-amines.

Reductive Aminations of Compounds 6, 7 and 8

The reductive aminations were accomplished by similar procedures. The sterol (500 mg for, compound 6.2 g for compounds 7 and 8) was dissolved in 2-propanol (25 mL). Ethylenediamine (1 mL) was added to the flask. The 3-oxo sterol and ethylenediamine were allowed to stir at room temperature for approximately four hours. Sodium cyanoborohydride (250 mg for compound 6 and 100 mg for compounds 7 and 8) was dissolved in 2-propanol (2 mL) and acetic acid (1 mL). The sodium cyanoborohydride solution was added to the reaction flask after evolution of gas had almost ceased (approximately five minutes). In all cases the reaction was complete before the first TLC was taken (less than five minutes). The work-up was the same for all analogues, solution was made basic (pH 10–11) by the addition of carbonate buffer. The aqueous layer was repeatedly extracted with chloroform. The chloroform was removed in vacuo and the crude 3-aminosteroid was dissolved in 10% acetonitrile/water, acidified with TFA. The solubility of compound I was very poor. The solutions were passed through a 45 g Gelman vacu-cap filter. The 3-aminosteroid isomers were separated by reverse phase chromatography on C18 (Dynamax, 300, 8 μM, 21.6 mm ID, 25 cm/L) using a gradient of acetonitrile in water with 0.1% TFA throughout. The separation of the sulfonamide—(G) and—(F) isomers was accomplished relatively easily, while only the—isomer of the methyl carbamate (H) was isolated cleanly. For the urea analogue the isomers were not effectively separated by chromatography on C18. The urea derivatives were submitted for biological testing as the mixed isomers (I).

Analytical for Compounds F, G, H, and I

Compound-F: $^1$H NMR (400 MHZ, $CD_3OD$): 0.74 (s, 3H), 0.89 (s, 3H), 1.04 (d, 3H, J=6.7 Hz), 2.75 (m, 1H), 2.94 (s, 3H), 3.1–3.3 (m, buried in solvent signal); MS (ES) $[M+H]^+$: 454; Anal. Calcd. for $C_{25}H_{47}N_3O_2S$-2TFA-0.8$H_2O$: C 50.03%, H 7.33%, N 6.04%. Found: C 49.98%, H 7.10%, N 6.00%.

Compound-G: $^1$H NMR (400 MHZ, $CD_3OD$): 0.74 (s, 3H), 0.88 (s, 3H), 1.02 (d, 3H, J=6.7 Hz), 2.75 (d of d, 1H, $J_1$=10 Hz, $J_2$=3 Hz), 2.94 (s, 3H), 3.15 (d of d, $J_1$=10 Hz, $J_2$=2 Hz), 3.48 (sharp m, 1H); MS (ES) $[M+H]^+$: 454; Anal. Calcd. for $C_{25}H_{47}N_3O_2S$-2TFA-0.8$H_2O$: C 50.03%, H 7.33%, N 6.04%. Found: C 50.23%, H 7.38%, N 6.05%.

Compound-H: $^1$H NMR (400 MHZ, $CD_3OD$): 0.74 (s, 3H), 0.90 (s, 3H), 0.97 (d, 3H, J=6.7 Hz), 2.75 (d of d, 1H, $J_1$=10 Hz, $J_2$=3 Hz), 3.20 (m, 2H), 3.66 (s, 3H); MS (FAB) $[M+H]^+$: 434; Anal. Calcd. for $C_{26}H_{47}N_3O_2$-2TFA-1.5$H_2O$: C 52.32%, H 7.61%, N 6.10%. Found: C 52.10%, H 7.31%, N 5.78%.

Compound-I: $^1$H NMR (400 MHZ, $CD_3OD$): 0.69 (s, 3H), 0.84 (s, 3H, 2 signals from the mixed isomers), 0.93 (d, 3H, J=6.7 Hz), 2.75 (m, 1H), 3.10–3.30 (m, buried in solvent peak), 3.45 (sharp m); MS (FAB) $[M+H]^+$: 474; Anal. Calcd. for $C_{29}H_{52}N_4O_1$-2TFA-2$H_2O$: C 53.79%, H 7.93%, N 7.60%. Found: C 53.91%, H 7.35%, N 7.74%.

EXAMPLE 8

3-Aminosteroid Analogues Prepared via the 22 Aldehyde

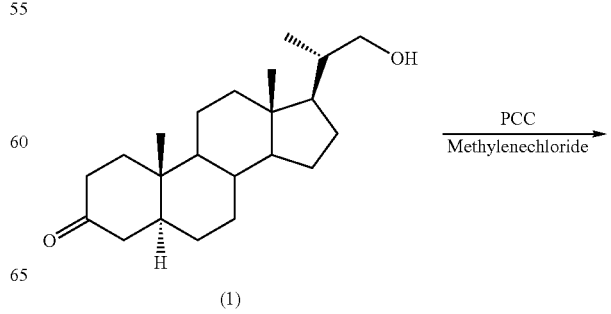

(1)

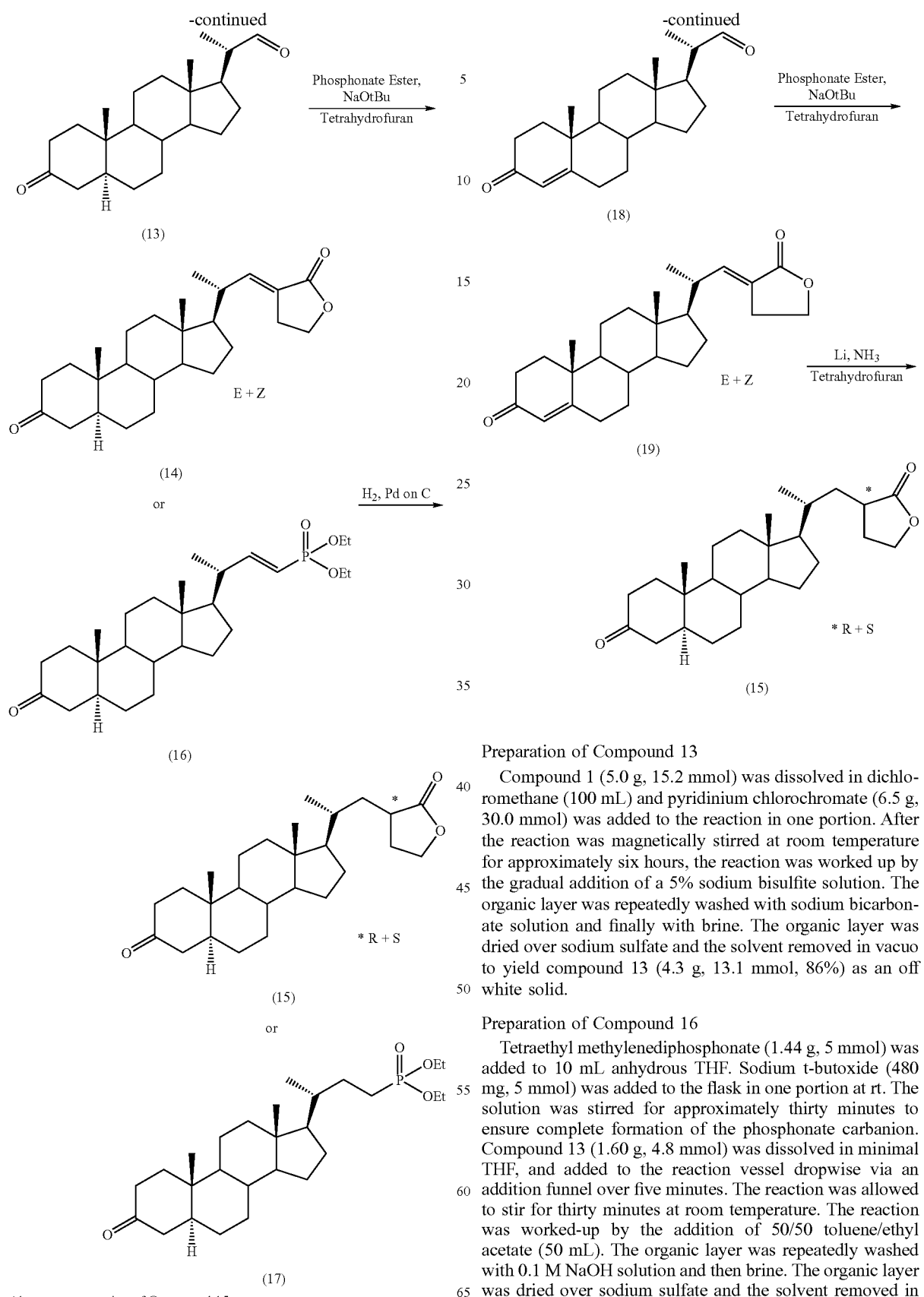

Preparation of Compound 13

Compound 1 (5.0 g, 15.2 mmol) was dissolved in dichloromethane (100 mL) and pyridinium chlorochromate (6.5 g, 30.0 mmol) was added to the reaction in one portion. After the reaction was magnetically stirred at room temperature for approximately six hours, the reaction was worked up by the gradual addition of a 5% sodium bisulfite solution. The organic layer was repeatedly washed with sodium bicarbonate solution and finally with brine. The organic layer was dried over sodium sulfate and the solvent removed in vacuo to yield compound 13 (4.3 g, 13.1 mmol, 86%) as an off white solid.

Preparation of Compound 16

Tetraethyl methylenediphosphonate (1.44 g, 5 mmol) was added to 10 mL anhydrous THF. Sodium t-butoxide (480 mg, 5 mmol) was added to the flask in one portion at rt. The solution was stirred for approximately thirty minutes to ensure complete formation of the phosphonate carbanion. Compound 13 (1.60 g, 4.8 mmol) was dissolved in minimal THF, and added to the reaction vessel dropwise via an addition funnel over five minutes. The reaction was allowed to stir for thirty minutes at room temperature. The reaction was worked-up by the addition of 50/50 toluene/ethyl acetate (50 mL). The organic layer was repeatedly washed with 0.1 M NaOH solution and then brine. The organic layer was dried over sodium sulfate and the solvent removed in vacuo to yield compound 16 (1.48 g, 3.2 mmol, 67%) as a white crystalline solid.

Preparation of Compound 17

Compound 16 (1.48 g, 3.2 mmol) was dissolved ethyl acetate (50 mL) and added to Parr flask. The flask was purged with nitrogen and 5% palladium on carbon (280 mg) was added to the flask. The flask was evacuated and filled with $H_2$ at 50 psi. The flask was shaken at room temperature overnight (approximately fourteen hours). The reaction was worked-up by filtering through a bed of Celite-7® and thoroughly washing the filter cake with ethyl acetate. The filtrate was evaporated in vacuo to give compound 17 as a white crystalline solid (1.41 g, 3.1 mmol, 97%).

Preparation of Compound 19

The phosphonate carbanion was prepared by the addition of 2-(diethylphosphono)-butyrolactone (25 g, 120 mmol) (prepared by heating a neat mixture of 2-bromobutyrolactone and triethylphosphite) to THF (1.2 L). Sodium tert-butoxide (11.5 g, 120 mmol) was added with ice bath cooling. The reaction was allowed to warm to room temperature over thirty minutes to insure complete formation of the phosphonate carbanion. Compound 18 (25.0 g, 76.2 mmol) was dissolved in THF (200 mL) and added to the reaction mixture, which was then warmed to reflux for approximately sixteen hours. The reaction was worked-up by removal of some THF (~700 mL) in vacuo. Toluene (500 mL) was then added and the solution washed repeatedly with 0.1 M NaOH solution and then brine. The organic layer was dried over sodium sulfate and the solvent removed in vacuo. The resulting solid was recrystallized from hexane/ethyl acetate to yield the mixed E,Z-isomers 19 as an off white solid (25.7 g, 64.5 mmol, 85%).

Preparation of Compound 15

Compound 19 (23.0 g, 57.8 mmol) was dissolved in THF/toluene 3/1 (1 L). The solution was then added to ammonia (1.2 L) at −78° C. Lithium wire was added to the reaction until a deep blue color persisted. The reaction was warmed to reflux for thirty minutes, chilled back to −78° C., and then quenched by the addition of ammonium chloride. The ammonia was allowed to boil off overnight. The residue was acidified by the addition of 1.0 M HCl solution (500 mL) with aggressive stirring and an additional portion of toluene (500 mL) was added. There was a significant amount of insoluble material at the organic aqueous interface so the material was filtered through Celite-7®. The filtrate was added to a separatory funnel and the organic layer was washed with repeatedly with 0.1 M HCl, followed by sodium bicarbonate solution and brine. The organic layer was dried over sodium sulfate and the solvent removed in vacuo to yield compound 15 as a mixture of isomers at C23 (14.3 g, 36.2 mmol, 63%).

Reductive Aminations of Compounds 15 and 17

Figure 5:
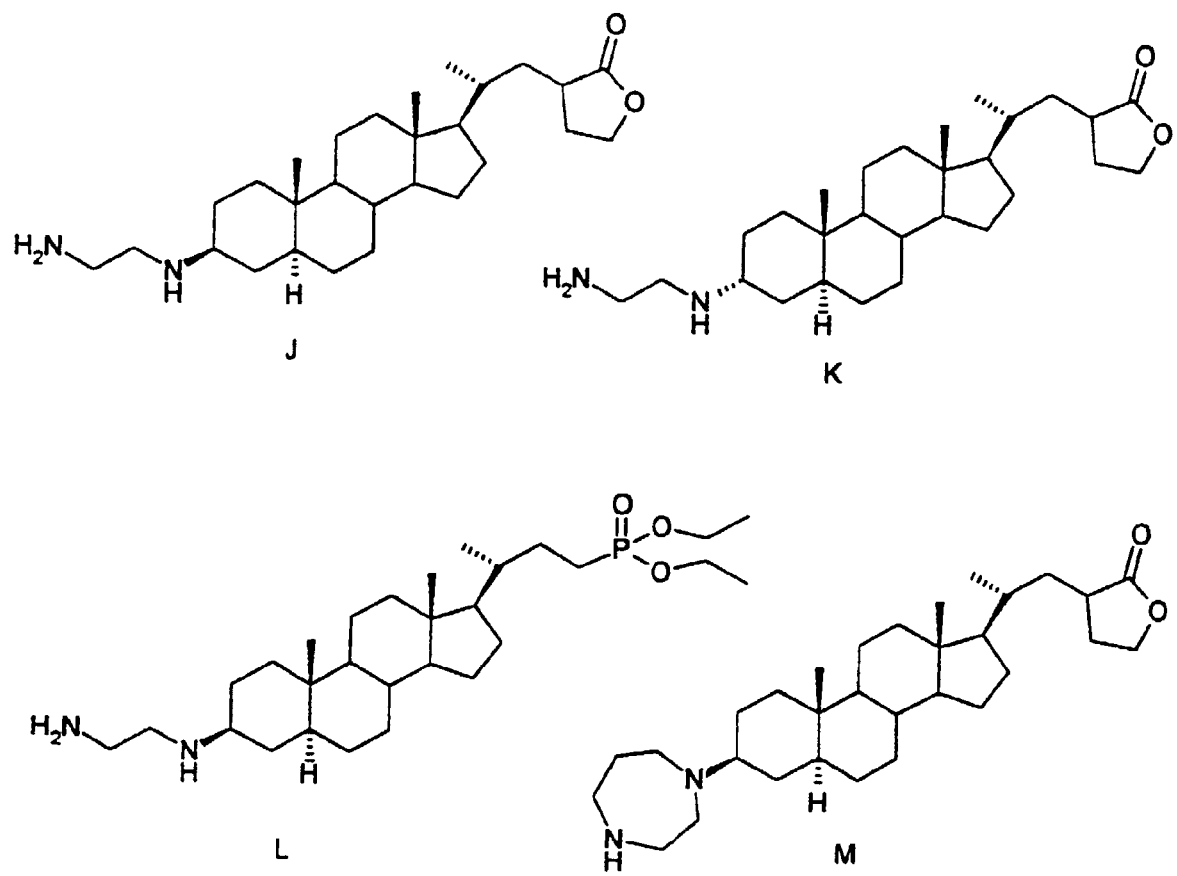
FIG. 5: 3-aminosteroid analogues prepared via the 22-aldehyde.
Figure 6:
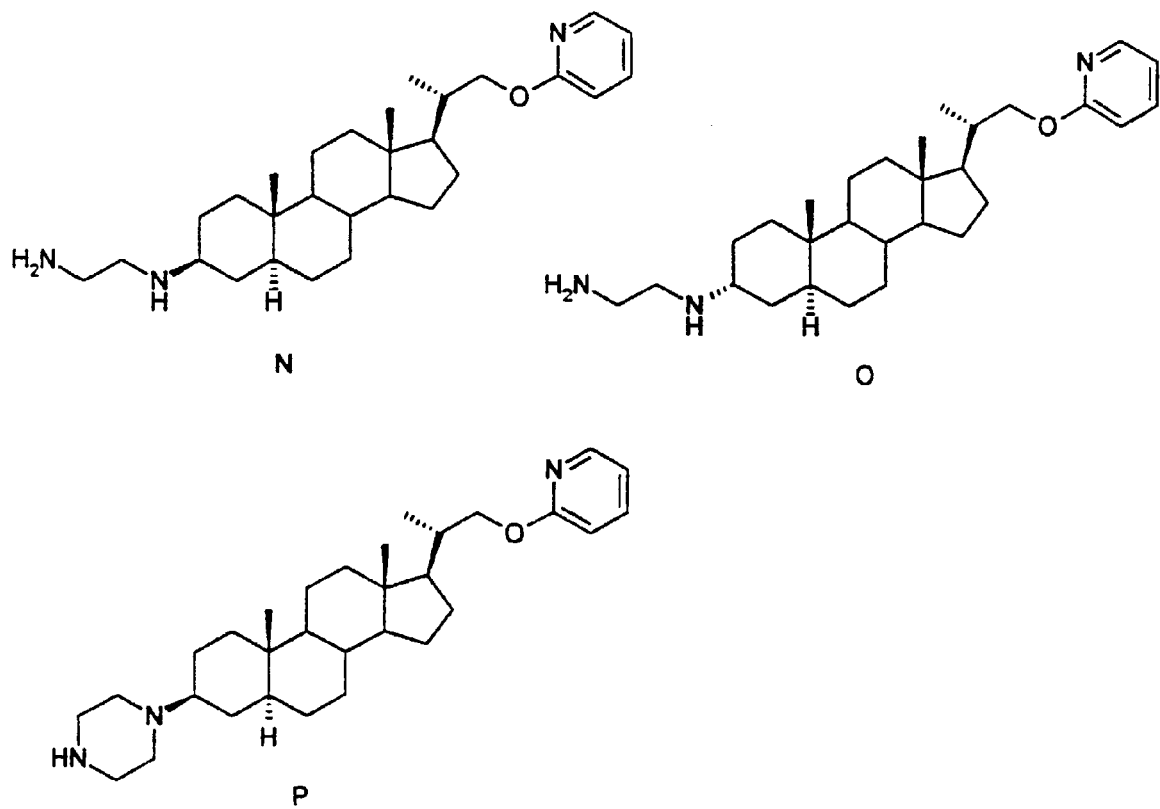
FIG. 6: 3-aminosteroids prepared via the Mitsunobu reaction.

The 3-aminosteroid analogues prepared from compounds 15 and 17, compounds J, K, L and M are depicted in FIG. 5. The reactions and isolations for these compounds were all virtually identical to those described previously for the preparation of compounds F, G, H and I. The only changes being the scale at which various preparations were run and the polyamine which was used; ethylenediamine was replaced with homopiperazine in one case (Compound-M).

Analytical for Compounds J, K, L and M

Compound-J: $^1$H NMR (400 MHZ, $CD_3OD$): 0.74 (s, 3H), 0.90 (s, 3H), 1.04 (d, 3H, J=6.7 Hz), 2.45 (m, 1H), 2.64 (m, 1H), 3.17 (m, 1H) 3.68 (m, 1H), 4.21 (m,1H), 4.30 (m,1H); MS (FAB) [M+H]$^+$: 445; Anal. Calcd. for $C_{28}H_{48}N_2O_2$-2TFA-1.0$H_2O$: C 55.64%, H 7.59%, N 4.06%. Found: C 55.75%, H 7.41%, N 4.17%.

Compound-K: $^1$H NMR (400 MHZ, DMSO-$d_6$): 0.74 (s, 3H), 0.90 (s, 3H), 1.04 (d, 3H, J=6.7 Hz), 2.35 (m, 1H), 2.60 (m, 1H), 3.17 (sharp m, 4H), 4.12 (m, 1H), 4.26 (m,1H); MS (FAB) [M+H]$^+$: 445; Anal. Calcd. for $C_{28}H_{48}N_2O_2$-2TFA-1.0$H_2O$: C 55.64%, H 7.59%, N 4.06%. Found: C 55.43%, H 7.63%, N 4.10%.

Compound-L: $^1$H NMR (400 MHZ, DMSO-$d_6$): 0.72 (s, 3H), 0.80 (s, 3H), 0.94 (d, 3H, J=6.7 Hz), 1.21 (t, 6H, J=6.7 Hz), 3.10–3.25 (m, 4H), 3.95 (d of q, 4H, $J_1$=6.7 Hz, $J_2$=2 Hz); MS (FAB) [M+H]$^+$: 511; Anal. Calcd. for $C_{29}H_{55}N_2O_3P$-2TFA-1.0$H_2O$: C 52.37%, H 7.86%, N 3.70%. Found: C 52.58%, H 7.82%, N 3.53%.

Compound-M: $^1$H NMR (400 MHZ, DMSO-$d_6$): 0.72 (s, 3H), 0.79 (s, 3H, 2 signals from mixed diastereomers), 0.94 (d, 3H, J=6.7 Hz, 2 signals), 2.31 (m, 1H), 2.55 (m, 1H), 3.15–3.72 (m, 8H), 4.10 (m, 1H), 4.26 (m, 1H); MS (FAB) [M+H]$^+$: 485; Anal. Calcd. for $C_{31}H_{52}N_2O_2$-2TFA-2.0$H_2O$: C 56.14%, H 7.81%, N 3.74%. Found: C 56.34%, H 7.14%, N 3.79%.

EXAMPLE 9

3-Aminosteroids Prepared via Mitsunobu Reaction with Compound 1

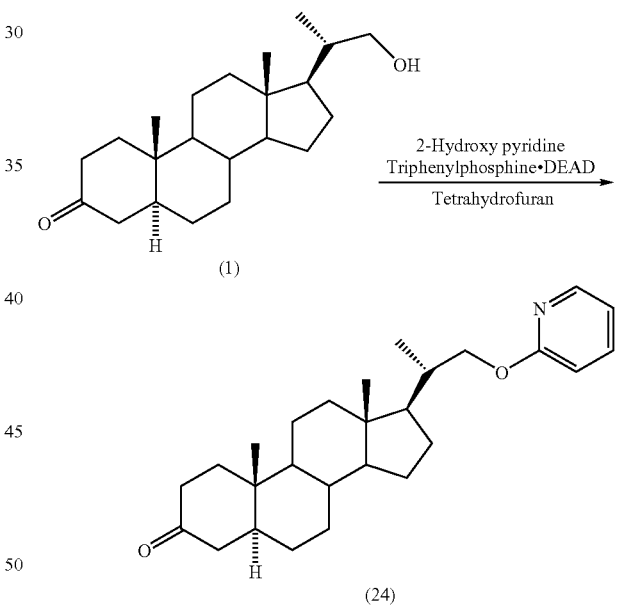

Preparation of Compound 24

Compound 1 (5.0 g, 15.0 mmol) was dissolved in anhydrous THF (75 mL), and was treated with 2-hydroxypyridine (1.7 g, 18.0 mmol) and triphenylphosphine (4.7 g, 18.0 mmol). Diethylazodicarboxylate, DEAD, (3.1 g, 18.0 mmol) was added to the flask dropwise via an addition funnel. The addition of the DEAD caused an exothermic reaction. The reaction was allowed to stir at room temperature for thirty minutes before the solution was reduced in volume and applied directly to a 6×10 cm silica gel column (elution with 20% ethyl acetate in toluene). The fractions containing pure compound 24 were pooled and the solvent removed in vacuo to yield a white crystalline solid (3.7 g, 9.1 mmol, 61%).

EXAMPLE 10

Preparation of Compounds N, O, and P

Compounds N, O, and P (FIG. 6) were prepared by the same reductive amination procedure described previously.

Analytical for Compounds N, O and P

Compound-N: $^1$H NMR (400 MHZ, CD$_3$OD): 0.69 (s, 3H), 0.83 (s, 3H), 1.05 (d, 3H, J=6.7 Hz), 3.14 (m, 4H), 3.96 (d of d, 1H, J$_1$=10 Hz, J$_2$=2 Hz), 4.24 (d of d, 1H, J$_1$=10 Hz, J$_2$=3 Hz), 6.70 (m,1H), 6.86 (m,1H), 7.60 (m,1H), 8.14 (m,1H); MS(+FAB): [M+H]$^+$454; Anal. Calcd. for C$_{29}$H$_{47}$N$_3$O-2TFA-3H$_2$O: C 53.87%, H 7.53%, N 5.71%. Found: C 53.72%, H 6.61%, N 5.85%.

Compound-O: $^1$H NMR (400 MHZ, DMSO-d$_6$): 0.70 (s, 3H), 0.81 (s, 3H), 1.07 (d, 3H, J=6.7 Hz), 3.15 (m, 4H), 3.94 (d of d, 1H, J$_1$=10 Hz, J$_2$=2 Hz), 4.25 (d of d, 1H, J$_1$=10 Hz, J$_2$=3 Hz), 6.70 (m, 1H), 6.85 (m, 1H), 7.60 (m, 1H), 8.14 (m, 1H); MS(+FAB): [M+H]$^+$454; Anal. Calcd. for C$_{29}$H$_{47}$N$_3$O-2TFA-3H$_2$O: C 55.22%, H 7.44%, N 5.85%. Found: C 55.12%, H 6.74%, N 5.95%.

Compound-P: $^1$H NMR (400 MHZ, DMSO-d$_6$): 0.70 (s, 3H), 0.81 (s, 3H), 1.14 (d, 3H, J=6.7 Hz), 2.90 (m, 4H), 4.04 (d of d, 1H, J$_1$=10 Hz, J$_2$=2 Hz), 4.25 (d of d, 1H, J$_1$=10 Hz, J$_2$=3 Hz), 6.70 (m, 1H), 6.85 (m, 1H), 7.60 (m, 1H), 8.14 (m, 1H); MS(+FAB): [M+H]$^+$480; Anal. Calcd. for C$_{29}$H$_{47}$N$_3$O-3TFA-1H$_2$O: C 52.92%, H 6.48%, N 5.00%. Found: C 53.18%, H 5.88%, N 4.22%.

EXAMPLE 11

Preparation of 24-Amide

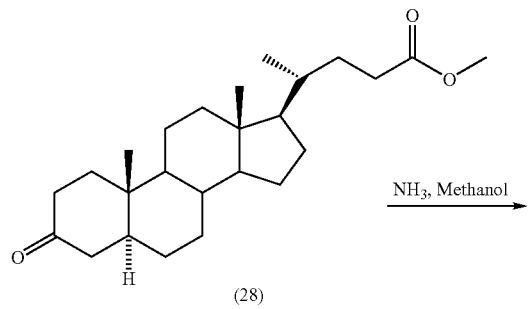

(28)

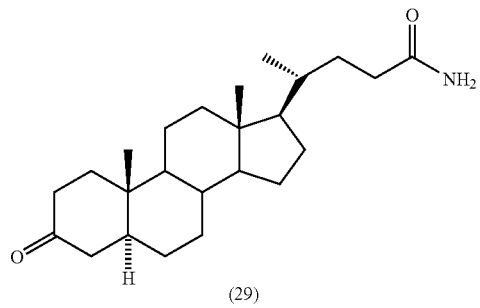

(29)

Preparation of Compound 29

Compound 28 (1.0 g, 2.6 mmol) was dissolved in methanol (50 mL). The solution was chilled to 0° C. and ammonia was bubbled into the reaction vessel for thirty minutes. The reaction was sealed and allowed to stir at room temperature for two weeks. The reaction was worked-up by chilling the reaction to −20° C., opening the sealed tube, and then allowing the reaction to warm to room temperature. After the excess ammonia had evaporated, the remainder of the methanolic ammonia was removed in vacuo to yield compound 29 (0.95 g, 2.5 mmol, 96%).

Figure 7:
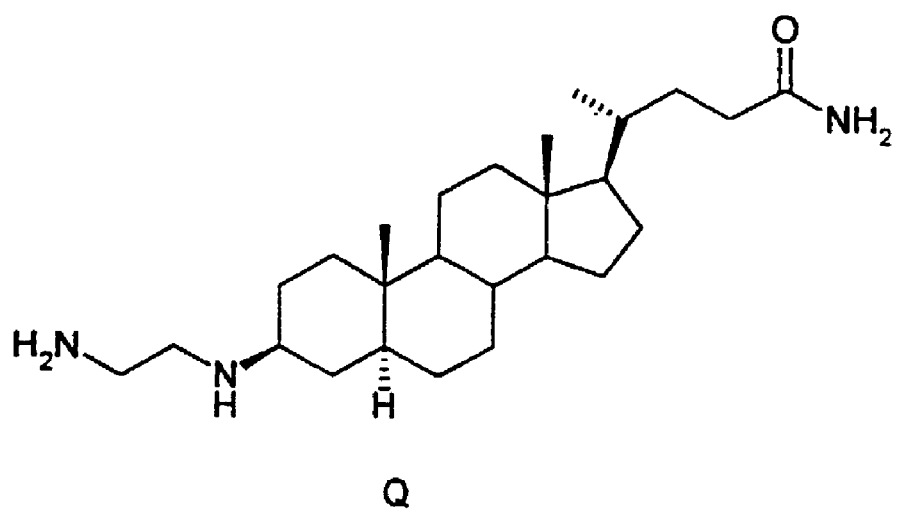
FIG. 7: 24-Amide 3-aminosteroid analogue.

Preparation of Compound-Q (FIG. 7)

The 3-aminosteroid analogue of compound 29 was prepared by same methods described earlier for the preparation of the other 3-aminosteroid analogues.

Compound-Q: $^1$H NMR (400 MHZ, CD$_3$OD): 0.74 (s, 3H), 0.93 (s, 3H), 0.98 (d, 3H, J=6.7 Hz), other downfield signals buried in the solvent peak; MS (+FAB): [M+H]$^+$418; Anal. Calcd. for C$_{29}$H$_{47}$N$_3$O-2TFA-0.7H$_2$O: C 54.73%, H 7.72%, N 6.38%. Found: C 54.70%, H 7.51%, N 6.18%.

While the invention has been described and illustrated herein by references to various specific materials, procedures and examples, it is understood that the invention is not restricted to the particular material combinations of material and procedures selected for that purpose. Numerous variations of such details can be implied as will be appreciated by those skilled in the art.

Other embodiments of the invention described above and will be apparent to those skilled in the art from consideration of the specification and practice of the invention disclosed within. All cited patents and publications referred to in this application are herein incorporated by reference in their entirety. It is intended that the specification and examples considered as exemplary only, with true scope and spirit of the invention being indicated by the following claims:

TABLE 1

| Structure | Aggregation Assay Minimum Effective Conc. (μg/mL) | PBMC Proliferation ASSAY IC50 (μg/mL) |
|---|---|---|
| code M | 10 | |
| code P | >10 | |
| code R | | 0.24 |
| code S | 10 | <0.1 (toxic) |

TABLE 1-continued

| Structure | Aggregation Assay Minimum Effective Conc. (μg/mL) | PBMC Proliferation ASSAY IC50 (μg/mL) |
|---|---|---|
| code T | 10, 5 | 2.77 |
| code U | 1–10 | 0.40 |
| code V | 10 | 0.41 |
| code O | 10 | 0.25 |

TABLE 1-continued
| Structure | Aggregation Assay Minimum Effective Conc. (µg/mL) | PBMC Proliferation ASSAY IC50 (µg/mL) |
|---|---|---|
| 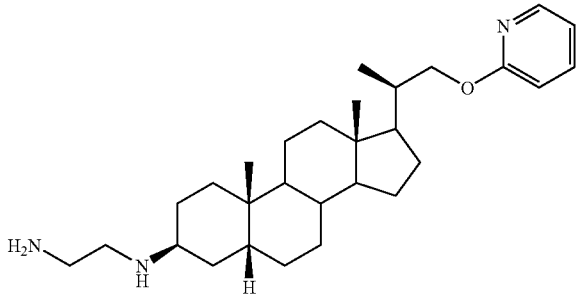<br>code N | 1–10 | 0.06 |
| 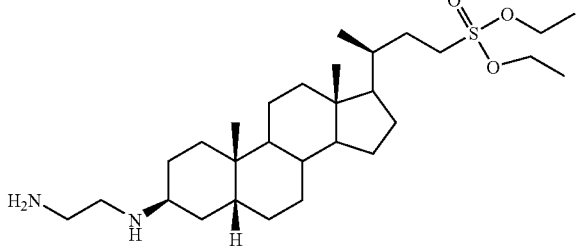<br>code L | 10 | 0.22 |
| 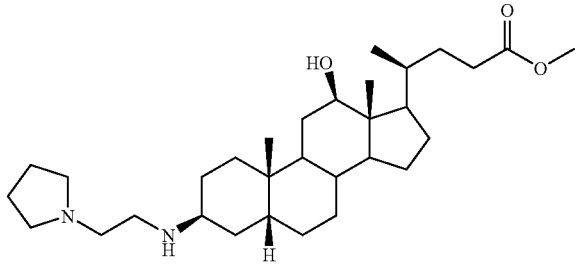<br>code W | 10 | |
| 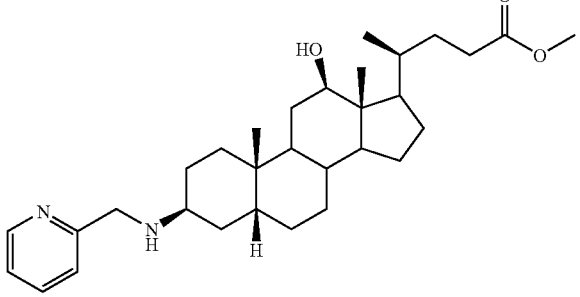<br>code X | 10 | |

TABLE 1-continued

| Structure | Aggregation Assay Minimum Effective Conc. (μg/mL) | PBMC Proliferation ASSAY IC50 (μg/mL) |
|---|---|---|
| code Y | 10 | |
| code G | 10 | |
| code F | 10, 5 | 2.88 |
| code Z | 10, 5 | 0.71 |

TABLE 1-continued

| Structure | Aggregation Assay Minimum Effective Conc. (µg/mL) | PBMC Proliferation ASSAY IC50 (µg/mL) |
|---|---|---|
| code AA | 10, 5 | 0.42 |
| code AB | 10, 5 | 2.54 |
| code AC | 10, 5 | 0.47 |
| code I | 10, 1 | 0.23 |

TABLE 1-continued

| Structure | Aggregation Assay Minimum Effective Conc. (μg/mL) | PBMC Proliferation ASSAY IC50 (μg/mL) |
|---|---|---|
| code O | 10, 5 | 2.42 |
| code AD | 10, 5 | 0.29 |
| code K | 10 (+/−), 5 | 0.31 |
| code H | 10, 0.5 | 0.26, 0.44 |

TABLE 1-continued

| Structure | Aggregation Assay Minimum Effective Conc. (µg/mL) | PBMC Proliferation ASSAY IC50 (µg/mL) |
|---|---|---|
| code J | 1 | 0.03 |
| code AE | 10, 5 | 0.28 |
| code AF | 10, 5 | 2.41 |
| code D | 10 | |

TABLE 1-continued

| Structure | Aggregation Assay Minimum Effective Conc. (μg/mL) | PBMC Proliferation ASSAY IC50 (μg/mL) |
|---|---|---|
| code A | 1 | |
| code AG | 10 | |
| code C | >10 | |
| code AH | 1 | 0.1 |

TABLE 1-continued

| Structure | Aggregation Assay Minimum Effective Conc. (μg/mL) | PBMC Proliferation ASSAY IC50 (μg/mL) |
|---|---|---|
| 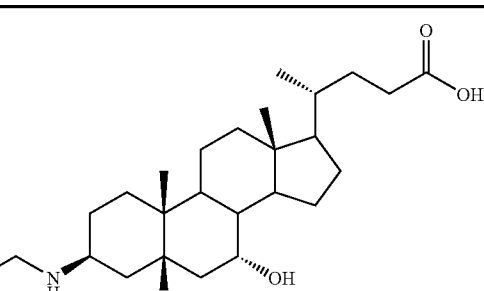 code E | >10 | |
| 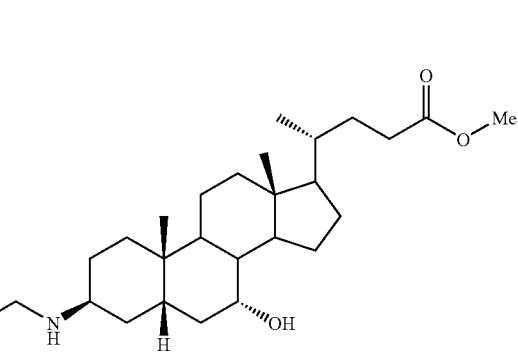 code B | 10, 5 | 0.41, 2.35, 0.75 |

What is claimed:

1. A compound having the formula:

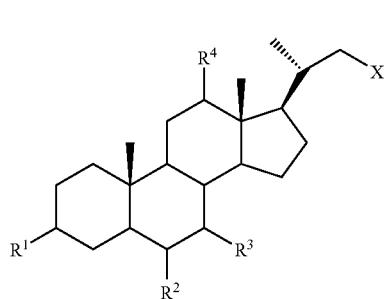

wherein X is selected from the group consisting of —CH$_2$—PO(OR$^5$)$_2$, —NH—SO$_2$—R$^5$, —NH—CO—OR$^5$, —CH$_2$—CO—NH$_2$, —CH$_2$—CO—NH—R$^8$, —CH$_2$—CO$_2$—R$^5$,

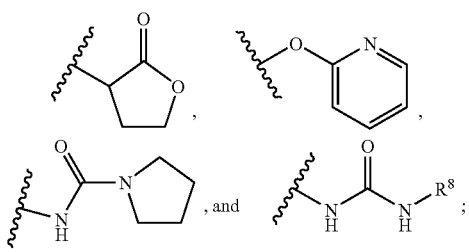

R$^1$ is selected from the group consisting of R$^6$—NH—,

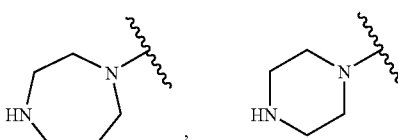

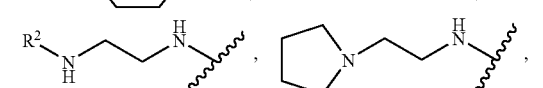

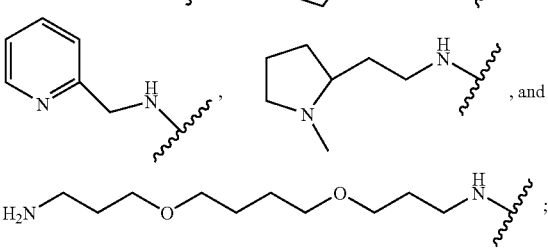

R$^2$, R$^3$, and R$^4$ are each independently selected from the group consisting of H, —OAc, and

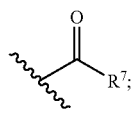

$R^5$ is a $C_{1-12}$ alkyl;

$R^6$ is selected from the group consisting of $C_{1-6}$ alkyl and phenyl; and $R^7$ and $R^8$ are each independently selected from the group consisting of H, $C_{1-6}$ alkyl and phenyl.

2. A method of treating atopic allergy in a mammal comprising administering an effective amount of a 3-aminosteroid compound, wherein said compound has the following chemical formula:

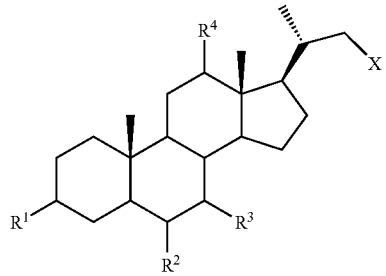

wherein X is selected from the group consisting of $-CH_2-PO(OR^5)_2$, $-NH-SO_2-R^5$, $-NH-CO-OR^5$, $-CH_2-CO-NH_2$, $-CH_2-CO-NH-R^8$, $-CH_2-CO_2-R^5$,

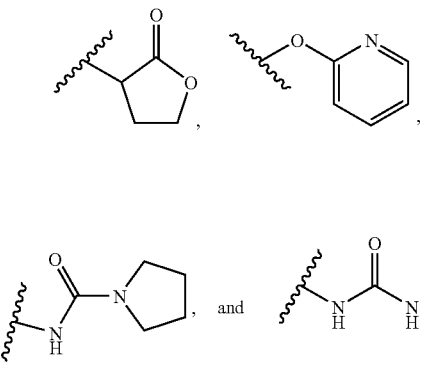

$R^1$ is selected from the group consisting of $R^6-NH-$,

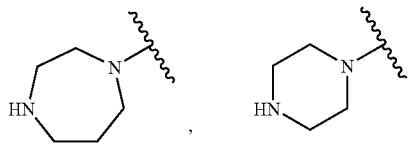

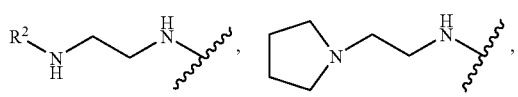

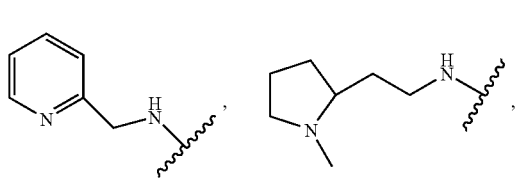

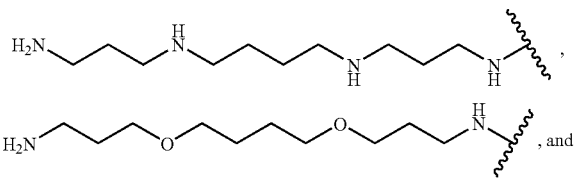

$R^2$, $R^3$, and $R^4$ are each independently selected from the group consisting of H, $-OAc$, and

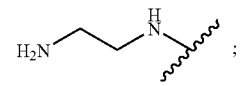

$R^5$ is a $C_{1-12}$ alkyl; and $R^6$, $R^7$ and $R^8$ are each independently selected from the group consisting of H, $C_{1-6}$alkyl, and phenyl.

3. The method of claim 2, wherein said compound has the following chemical formula

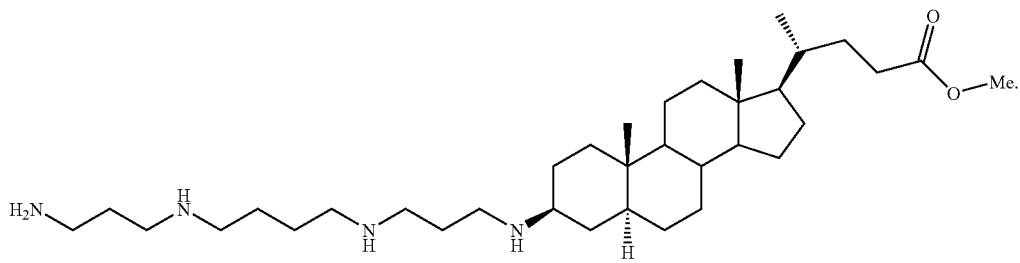

4. The method of claim 2, wherein said compound has the following chemical formula:

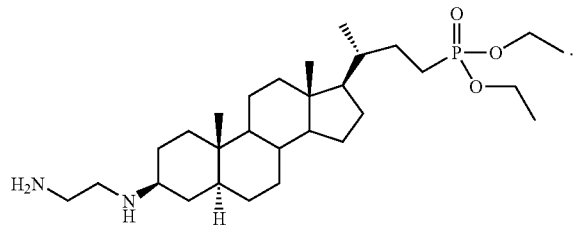

5. A method of treating asthma in a mammal comprising administering an effective amount of the 3-aminosteroid compound, wherein said compound has the following chemical formula:

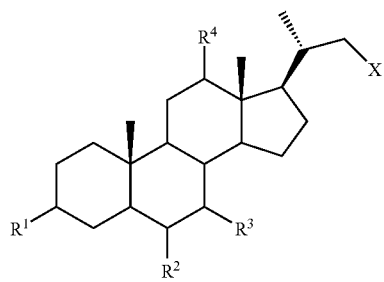

wherein X is selected from the group consisting of —$CH_2$—PO(OR$^5$)$_2$, —NH—SO$_2$—R$^5$, —NH—CO—OR$^5$, —$CH_2$—CO—NH$_2$, —$CH_2$—CO—NH—R$^8$, —$CH_2$—CO$_2$—R$^5$, $R^1$ is selected from the group consisting of $R^6$—NH—,

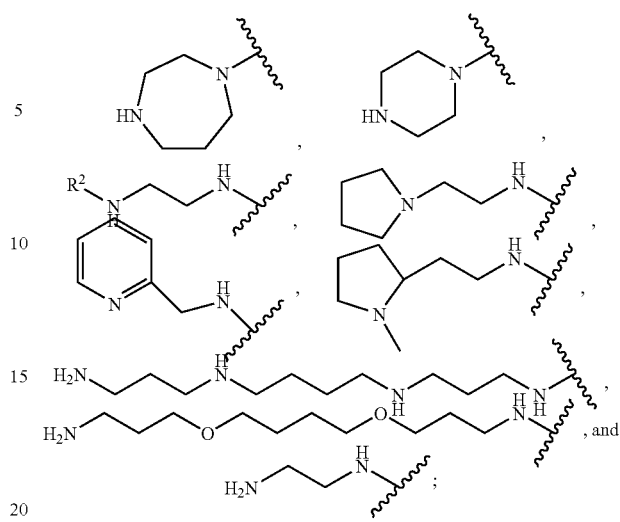

$R^2$, $R^3$, and $R^4$ are each independently selected from the group consisting of H, —OAc, and

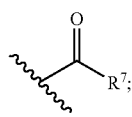

$R^5$ is a $C_{1-12}$ alkyl; and
$R^6$, $R^7$ and $R^8$ are each independently selected from the group consisting of H, $C_{1-6}$alkyl, and phenyl.

6. The method of claim 5, wherein said compound has the following chemical formula:

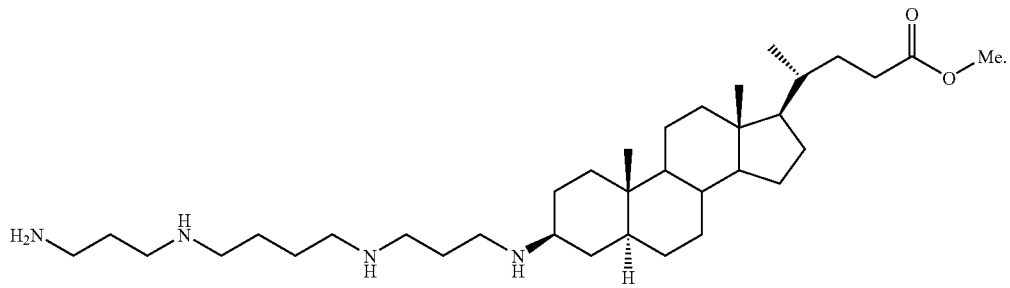

7. The method of claim 5, wherein said compound has the following chemical formula:

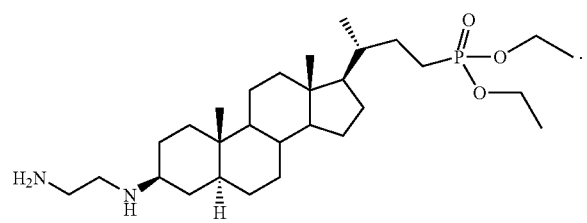

* * * * *

UNITED STATES PATENT AND TRADEMARK OFFICE
CERTIFICATE OF CORRECTION

PATENT NO.       : 7,074,778 B2                                              Page 1 of 2
APPLICATION NO.  : 10/148553
DATED            : July 11, 2006
INVENTOR(S)      : Roy C. Levitt et al.

It is certified that error appears in the above-identified patent and that said Letters Patent is hereby corrected as shown below:

Claim 1, column 46, line 45, 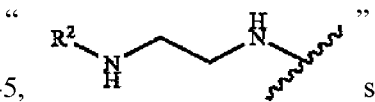 should be replaced by -- 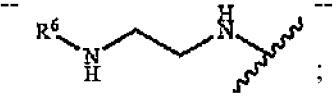 --;

Claim 1, column 46, line 50, delete "and";

Claim 1, column 46, line 56, add --, and 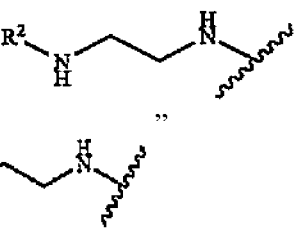 -- after " 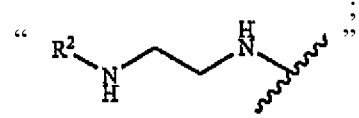 ";

Claim 2, column 48, line 11,  should be replaced by --  --;

UNITED STATES PATENT AND TRADEMARK OFFICE
CERTIFICATE OF CORRECTION

PATENT NO. : 7,074,778 B2
APPLICATION NO. : 10/148553
DATED : July 11, 2006
INVENTOR(S) : Roy C. Levitt et al.

It is certified that error appears in the above-identified patent and that said Letters Patent is hereby corrected as shown below:

Claim 5, column 50, line 7, " 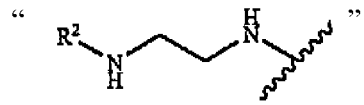 " should be replaced by

-- 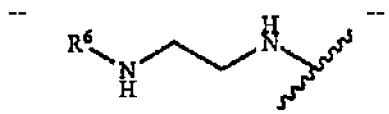 --.

Signed and Sealed this

Sixth Day of November, 2007

JON W. DUDAS
*Director of the United States Patent and Trademark Office*